US007999088B2

(12) United States Patent
Qiu et al.

(10) Patent No.: US 7,999,088 B2
(45) Date of Patent: Aug. 16, 2011

(54) METHODS AND COMPOSITIONS TO ELICIT MULTIVALENT IMMUNE RESPONSES AGAINST DOMINANT AND SUBDOMINANT EPITOPES, EXPRESSED ON CANCER CELLS AND TUMOR STROMA

(75) Inventors: Zhiyong Qiu, Los Angeles, CA (US); Adrian Ion Bot, Valencia, CA (US)

(73) Assignee: MannKind Corporation, Valencia, CA (US)

( * ) Notice: Subject to any disclaimer, the term of this patent is extended or adjusted under 35 U.S.C. 154(b) by 0 days.

(21) Appl. No.: 11/454,616

(22) Filed: Jun. 16, 2006

(65) Prior Publication Data

US 2007/0004662 A1    Jan. 4, 2007

Related U.S. Application Data

(60) Provisional application No. 60/691,579, filed on Jun. 17, 2005.

(51) Int. Cl.
*C07H 21/02* (2006.01)
*C12K 15/11* (2006.01)

(52) U.S. Cl. ......................................... 536/23.1; 514/44
(58) Field of Classification Search ........................ None
See application file for complete search history.

(56) References Cited

U.S. PATENT DOCUMENTS

| | | | |
|---|---|---|---|
| 5,512,437 A | 4/1996 | Gaugler et al. | |
| 5,512,444 A | 4/1996 | Patard et al. | |
| 5,538,866 A | 7/1996 | Israeli et al. | |
| 5,571,711 A | 11/1996 | van der Bruggen et al. | |
| 5,589,466 A | 12/1996 | Felgner et al. | |
| 5,610,013 A | 3/1997 | Van den Eynde et al. | |
| 5,620,886 A | 4/1997 | Brichard et al. | |
| 5,648,226 A | 7/1997 | Van den Eynde et al. | |
| 5,679,647 A | 10/1997 | Carson et al. | |
| 5,683,886 A | 11/1997 | van der Bruggen et al. | |
| 5,747,271 A | 5/1998 | Boon-Falleur et al. | |
| 5,763,155 A | 6/1998 | Boon-Falleur et al. | |
| 5,763,165 A | 6/1998 | Boon-Falleur et al. | |
| 5,801,005 A | 9/1998 | Cheever et al. | |
| 5,804,381 A | 9/1998 | Chen et al. | |
| 5,830,753 A | 11/1998 | Coulie et al. | |
| 5,837,476 A | 11/1998 | Brichard et al. | |
| 5,840,839 A | 11/1998 | Wang et al. | |
| 5,844,075 A | 12/1998 | Kawakami et al. | |
| 5,856,136 A | 1/1999 | Au-Young | |
| 5,858,689 A | 1/1999 | van der Bruggen et al. | |
| 5,874,560 A | 2/1999 | Kawakami et al. | |
| 5,888,751 A | 3/1999 | Tureci et al. | |
| 5,935,818 A | 8/1999 | Israeli et al. | |
| 5,985,571 A | 11/1999 | Van Baren et al. | |
| 5,994,523 A | 11/1999 | Kawakami et al. | |
| 6,013,481 A | 1/2000 | DeBacker et al. | |
| 6,017,716 A | 1/2000 | Pfreundschuh | |
| 6,020,134 A | 2/2000 | Pfreundschuh | |
| 6,022,692 A | 2/2000 | Coulie et al. | |
| 6,025,191 A | 2/2000 | Pfreundschuh | |
| 6,025,470 A | 2/2000 | Valmori et al. | |
| 6,069,001 A | 5/2000 | Van den Eynde et al. | |
| 6,140,050 A | 10/2000 | Sahin et al. | |
| 6,174,692 B1 | 1/2001 | Rimoldi et al. | |
| 6,200,765 B1 | 3/2001 | Murphy et al. | |
| 6,274,145 B1 | 8/2001 | Chen et al. | |
| 6,287,756 B1 | 9/2001 | Tureci et al. | |
| 6,338,947 B1 | 1/2002 | Sahin et al. | |
| 6,342,221 B1 | 1/2002 | Thorpe et al. | |
| 6,417,165 B1 | 7/2002 | Valmori et al. | |
| 6,548,064 B1 | 4/2003 | Tureci et al. | |
| 6,605,711 B1 | 8/2003 | Valmori et al. | |
| 6,660,276 B1 | 12/2003 | Slingluff et al. | |
| 6,685,947 B1 | 2/2004 | Jackson et al. | |
| 6,709,844 B1 | 3/2004 | Levy | |
| 6,720,146 B2 * | 4/2004 | Stolk et al. ........................ 435/6 |
| 6,746,839 B1 | 6/2004 | Duff et al. | |
| 6,861,234 B1 | 3/2005 | Simard et al. | |
| 6,977,074 B2 | 12/2005 | Kundig et al. | |
| 6,994,851 B1 | 2/2006 | Kündig et al. | |
| 7,232,682 B2 | 6/2007 | Simard et al. | |
| 7,252,824 B2 | 8/2007 | Simard et al. | |
| 7,364,729 B2 | 4/2008 | Kundig et al. | |
| 7,390,654 B2 | 6/2008 | Levy | |
| 7,511,118 B2 | 3/2009 | Liu et al. | |

(Continued)

FOREIGN PATENT DOCUMENTS

NZ    564359    12/2006

(Continued)

OTHER PUBLICATIONS

Kessler et al., "Efficient Identification of Novel HLA-A (*)0201-presented cytotoxic T lymphocyte epitopes in the widely expressed tumor antigen PRAME by proteasome-mediated digestion analysis," *Journal of Experimental Medicine*, vol. 193, No. 1, pp. 73-88, Jan. 1, 2001. Notification of Transmittal of the International Search Report and the Written Opinion of the International Searching Authority, or the Declaration dated Dec. 4, 2006 for PCT/US2006/023498.

Bot A, "Potent Immunity Achieved by Targeted Sequential Administration of Recombinant DN Vectors and Anchor-Modified Epitope Peptides," Scient. Meeting of Int'l Society for Biological Therapy of Cancer. Retrieved from http://ww.isbtc.org/meetings/am05/presentations/bot.pdf (retrieved 2006), 2005.

Bot et al. "A Novel Class of Biotherapeutics Co-Targeting Cancer Cells and the Associated Tumor Neovasculature," J. of Immunotherapy, 28(6):637, 2005.

(Continued)

*Primary Examiner* — Sean E Aeder
(74) *Attorney, Agent, or Firm* — Davis Wright Tremaine LLP

(57) ABSTRACT

The present invention provides a method of treating cancer by providing to a subject in need thereof an immunogenic composition comprising a nucleic acid construct encoding a polypeptide comprising CTL epitopes $PSMA_{288-297}$ and $PRAME_{425-433}$, or a cross-reactive analogue. In embodiments of the present invention there is provided methods and compositions for inducing, entraining, and/or amplifying the immune response to MHC class-I restricted epitopes of carcinoma antigens to generate an effective anti-cancer immune response.

72 Claims, 8 Drawing Sheets

U.S. PATENT DOCUMENTS

| | | |
|---|---|---|
| 7,511,119 B2 | 3/2009 | Liu et al. |
| 7,605,227 B2 | 10/2009 | Liu et al. |
| 2002/0007173 A1 | 1/2002 | Kundig et al. |
| 2003/0044813 A1 | 3/2003 | Old et al. |
| 2003/0046714 A1 | 3/2003 | Simard et al. |
| 2003/0138808 A1 | 7/2003 | Simard et al. |
| 2003/0165834 A1 | 9/2003 | Chen et al. |
| 2003/0180298 A1 | 9/2003 | Old et al. |
| 2003/0180949 A1 | 9/2003 | Levy |
| 2003/0186355 A1 | 10/2003 | Ossendorp et al. |
| 2003/0215425 A1 | 11/2003 | Simard et al. |
| 2003/0220239 A1 | 11/2003 | Simard et al. |
| 2003/0228634 A1 | 12/2003 | Simard et al. |
| 2004/0063120 A1 | 4/2004 | Beer et al. |
| 2004/0132088 A1 | 7/2004 | Simard et al. |
| 2004/0180354 A1 | 9/2004 | Simard et al. |
| 2004/0203051 A1 | 10/2004 | Simard et al. |
| 2004/0253218 A1 | 12/2004 | Eisenbach-Schwartz et al. |
| 2005/0069982 A1 | 3/2005 | Simard et al. |
| 2005/0079152 A1 | 4/2005 | Bot et al. |
| 2005/0118186 A1 | 6/2005 | Chiang et al. |
| 2005/0130920 A1 | 6/2005 | Simard et al. |
| 2005/0142144 A1 | 6/2005 | Simard et al. |
| 2005/0221440 A1 | 10/2005 | Simard et al. |
| 2005/0260234 A1 | 11/2005 | Simard et al. |
| 2005/0287068 A1 | 12/2005 | Bot et al. |
| 2006/0008468 A1 | 1/2006 | Chiang et al. |
| 2006/0057673 A1 | 3/2006 | Liu et al. |
| 2006/0063913 A1 | 3/2006 | Liu et al. |
| 2006/0094661 A1 | 5/2006 | Liu et al. |
| 2006/0153844 A1 | 7/2006 | Kündig et al. |
| 2006/0153858 A1 | 7/2006 | Kundig et al. |
| 2006/0159689 A1 | 7/2006 | Chiang et al. |
| 2006/0159694 A1 | 7/2006 | Chiang et al. |
| 2006/0165711 A1 | 7/2006 | Bot et al. |
| 2006/0269521 A1 | 11/2006 | Levy |
| 2007/0003563 A1 | 1/2007 | Bot et al. |
| 2007/0004662 A1 | 1/2007 | Qiu et al. |
| 2007/0049533 A1 | 3/2007 | Liu et al. |
| 2007/0060518 A1 | 3/2007 | Liu et al. |
| 2007/0060524 A1 | 3/2007 | Liu et al. |
| 2007/0184062 A1* | 8/2007 | Simard et al. .............. 424/185.1 |
| 2007/0269464 A1 | 11/2007 | Simard et al. |
| 2008/0014211 A1 | 1/2008 | Bot et al. |
| 2008/0124352 A1 | 5/2008 | Diamond et al. |
| 2008/0199485 A1 | 8/2008 | Kundig et al. |
| 2009/0035252 A1 | 2/2009 | Kundig et al. |
| 2009/0131355 A1 | 5/2009 | Bot et al. |
| 2009/0148478 A1 | 6/2009 | Chiang et al. |
| 2009/0208537 A1 | 8/2009 | Simard et al. |
| 2009/0285843 A1 | 11/2009 | Simard et al. |

FOREIGN PATENT DOCUMENTS

| | | |
|---|---|---|
| NZ | 564360 | 12/2006 |
| WO | WO 97/04802 A1 | 2/1998 |
| WO | WO 98/58956 | 12/1998 |
| WO | WO 99/02183 | 1/1999 |
| WO | WO 99/43801 | 9/1999 |
| WO | WO 00/06723 | 2/2000 |
| WO | WO 00/20027 * | 4/2000 |
| WO | WO 01/30382 | 5/2001 |
| WO | WO 01/45728 | 6/2001 |
| WO | WO 01/62776 A1 * | 8/2001 |
| WO | WO 01/85932 | 11/2001 |
| WO | WO 01/90197 | 11/2001 |
| WO | WO 02/08716 | 1/2002 |
| WO | WO 02/28429 | 4/2002 |
| WO | WO 02/069907 | 9/2002 |
| WO | WO 02/069907 A2 | 9/2002 |
| WO | WO 02/081646 | 10/2002 |
| WO | WO 02/081646 A2 * | 10/2002 |
| WO | WO 02/102299 | 12/2002 |
| WO | WO 03/011331 | 2/2003 |
| WO | WO 03/011332 | 2/2003 |
| WO | WO 03/075952 | 9/2003 |
| WO | WO 03/076585 | 9/2003 |
| WO | WO 2004/018666 | 3/2004 |
| WO | WO 2004/022709 A2 | 3/2004 |
| WO | WO 2004/110485 | 12/2004 |
| WO | WO 2004/112825 | 12/2004 |
| WO | WO 2004/112825 A2 * | 12/2004 |
| WO | WO 2005/002621 A2 | 1/2005 |
| WO | WO 2005/010190 | 2/2005 |
| WO | WO 2006/009920 | 1/2006 |
| WO | WO 2006/014579 | 2/2006 |

OTHER PUBLICATIONS

Chang, SS. et al., "Prostate-specific Membrane Antigen Is Produced in Tumor-Associated Neovasculature," Clinical Cancer Research 5(10):2674-2681, 1999.

Fetsch, PA. et al., "Melanoma-associated antigen recognized by T cells (MART-1): the advent of a preferred immunocytochemical antibody for the diagnosis of metastatic malignant melanoma with fine-needle aspiration," Cancer 87:37-42, 1999.

Ghadersohi, et al., "Tumor Antigens and Markers for Breast and Ovarian Cancers," Frontiers in Bioscience 7:e48-57, 2002.

Horiguchi, et al., "Screening of HLA-A24-restricted Epitope Peptides from Prostate-Specific Membrane Antigen That Induce Specific Antitumor Cytotoxic T Lymphocytes," Clinical Cancer Research 8:3885-3892, 2002.

Kirkin et al., "The Immunogenic properties of melanoma-associated antigens recognized by cytotoxic T lymphocytes," Exp Clin Immunogenet 15:19-32, 1998.

Lu, J. et al., "Multiepitope Trojan Antigen Peptide Vaccines for the Induction of Antitumor CTL and Th Immune Responses," J. Immunol., 172:4575-4582, 2004.

Matsushita, M. et al., "Preferentially expressed antigen of melanoma (PRAME) in the development of diagnostic therapeutic methods for hematological malignancies," Leukemia & Lymphoma 44(3):439-444, 2003.

Moingeon, P. "Cancer Vaccines," Vaccine. 19(11-12):1305-1326, 2001.

Office Action for U.S. Appl. No. 10/292,413, filed Sep. 30, 2008.

Office Action for U.S. Appl. No. 10/657,022, (filed Sep. 5, 2003), dated Feb. 19, 2008.

Office Action for U.S. Appl. No. 10/871,707, (filed Jun. 17, 2004), dated Sep. 25, 2007.

Office Action for U.S. Appl. No. 10/871,708, (filed Jun. 17, 2004), dated Apr. 16, 2008.

Office Action for U.S. Appl. No. 10/895,523, (filed Jul. 20, 2004), dated Nov. 25, 2009.

Office Action for U.S. Appl. No. 10/896,325, (filed Jul. 20, 2004), dated Mar. 26, 2008.

Office Action for U.S. Appl. No. 11/067,064, (filed Feb. 25, 2005), dated Jan. 22, 2010.

Office Action for U.S. Appl. No. 11/067,159, (filed Feb. 25, 2005), dated Nov. 19, 2008.

Office Action for U.S. Appl. No. 11/073,347, (filed Jun. 30, 2005), dated Feb. 19, 2010.

Office Action for U.S. Appl. No. 11/323,049, (filed Dec. 29, 2005), dated Mar. 5, 2009.

Office Action for U.S. Appl. No. 11/323,572, (filed Dec. 29, 2005), dated May 22, 2009.

Office Action for U.S. Appl. No. 11/454,633, (filed Jun. 16, 2006), dated Apr. 10, 2007.

Office Action for U.S. Appl. No. 11/455,278, (filed Jun. 16, 2006), dated Mar. 14, 2008.

Office Action for U.S. Appl. No. 11/455,279, (filed Jun. 16, 2006), dated Dec. 23, 2009.

Office Action for U.S. Appl. No. 11/772,811, (filed Jul. 2, 2007), dated Nov. 4, 2009.

Office Action for U.S. Appl. No. 12/194,478, (filed Aug. 19, 2008), dated Jan. 29, 2010.

Office Action for U.S. Appl. No. 12/253,213, (filed Oct. 16, 2006), dated Sep. 2, 2009.

Reynolds, et al., "Identification of HLA-A*03, A*11 and B*07-restricted melanoma-associated peptides that are immunogenic in vivo by vaccine-induced immune response (VIIR) analysis," J Immunological Methods 244:59-67, 2000.

Scanlan et al., "Cancer/testis antigens: an expanding family of targets for cancer immunotherapy," Immunological Reviews 188:22-32, 2002.
Smith et al., "Human Dendritic Cells Genetically Engineered to Express a Melanoma Polyepitope DNA Vaccine Induce Multiple Cytotoxic T-Cell Responses," Clin Cancer Res, 7: 4253-4261, 2001.
Tajeddine, et al., "Tumor-associated antigen preferentially expressed antigen of melanoma (PRAME) induces caspase-independent cell death in vitro and reduces tumorigenicity in vivo," Cancer Research. 65(16):7348-7355, 2005.
U.S. Appl. No. 08/988,320, filed Dec. 10, 1997, Kundig.
U.S. Appl. No. 09/560,465, filed Apr. 28, 2000, Simard.
U.S. Appl. No. 09/561,571, filed Apr. 28, 2000, Simard, et al.
U.S. Appl. No. 09/561,572, filed Apr. 28, 2000, Simard, et al.
U.S. Appl. No. 09/999,186, filed Nov. 7, 2001, Simard, et al.
U.S. Appl. No. 10/005,905, filed Nov. 7, 2001, Simard, et al.
U.S. Appl. No. 10/896,325, filed Jul. 20, 2004, Simard, et al.
U.S. Appl. No. 11/323,520, filed Dec. 29, 2005, Diamond, et al.
U.S. Appl. No. 11/418,397, filed May 3, 2006, Kundig, et al.
U.S. Appl. No. 11/418,497, filed May 3, 2006, Kundig, et al.
U.S. Appl. No. 60/282,211, filed Apr. 6, 2001, Simard, et al.
U.S. Appl. No. 60/337,017, filed Nov. 7, 2001, Simard, et al.
U.S. Appl. No. 60/831,256, filed Jul. 14, 2006, Bot, et al.
U.S. Appl. No. 60/834,074, filed Jul. 28, 2006, Liu, et al.
U.S. Appl. No. 60/863,332, filed Oct. 27, 2006, Bot, et al.
U.S. Appl. No. 60/901,980, filed Feb. 15, 2007, Kundig, et al.
Ambrosini, G. et al., Nat. Med. 3:917-921, (1997).
Annex to Form PCT/ISA/206; Communication Relating to the Results of the Partial International Search Report for Application No. PCT/US2004/019546 dated Feb. 24, 2005.
Atkins, MB, et al., "High-Dose Recombinant Interleukin 2 Therapy for Patients With Metastatic Melanoma: Analysis of 270 Patients Treated Between 1985 and 1993," Journal of Clinical Oncology, 17(7): 2105, 1999.
Ayyoub et al. Cancer Res. 63(17): 5601-6 (2003).
Ayyoub et al. J. Immunol. 168(4): 1717-22 (2002).
Banat GA, et al., Cancer Immunol Immunother. Jan. 2001;49(11):573-86.
Baratin. J. Peptide Sci. 8:327-334 (2002).
Bergmann et al., J. Virology, 68(8): 5306-5310, 1994.
Berkow et al., Ed. The Merck Manual of Diagnosis and Therapy, 16th Ed., 1992, Rahway, NJ, Merck Res. Lab., p. 21.
Blanchet et al. J. Immunol. 167:5852-5861 (2001).
Borsi, L. et al. Exp. Cell Res. 199:98-105, (1992).
Brossart et al., J. Immunol. 1997, 158:3270-3276.
Carnemolla, B. et al. J. Cell Biol. 108:1139-1148, (1989).
Castellani, P. et al. Acta Neurochir. (Wien) 142:277-282, (2000).
Castellani, P. et al. Int. J. Cancer 59:612-618, (1994).
Cerundolo, et al. "Dendritic cells: a journey from laboratory to clinic." Nature Immunology. 5(1): 7-10 (2004).
Chang SS et al, Urology 57:801 (2001).
Chang, S.S. et al. "Five Different Anti-Prostate-Specific Membrane Antigen (PSMA) Antibodies Confirm PSMA Expression in Tumor Associated Neovasculature," Cancer Research, 59(13)3192-3198 (1999).
Chen, YT. "Identification of human tumor antigens by serological expression cloning: an online review on SEREX." Cancer Immun 2004 [updated Mar. 10, 2004; cited Apr. 1, 2004].
Chevalier, X. Br. J. Rheumatol. 35:407-415, (1996).
Chung et al. J. Immunother. 22:279-287 (1999).
Columbo et al, "Interleukin-12 in Anti-Tumor Immunity and Immunotherapy," Cytokine & Growth Factor Reviews, 13(2):155-168, 2002.
Courvalin, P. et al., Life Sci. 318:1207-1212, (1995).
Devito, et al. "Intranasal HIV-1-gp160-DNA/gp41 Peptide Prime-Boost Immunization Regimen in Mice Results in Long-Term HIV-1 Neutralizing Humoral Mucosal and Systemic Immunity." The Journal of Immunology. 173: 7078-7089 (2004).
Dhodapkar, et al. "Mature dendritic cells boost functionally superior CD8+ T-cell in humans without foreign helper epitopes." The Journal of Clinical Investigation. 105(6): R9-R14 (2000).
Di Fiore, et al., Science 237: 178-182, (1987).
Dietrich, G. et al., Biotechnology 16:181-185, (1998).

Dummer, R. et al., Dermatology 207: 116-118, 2003.
Eisenlohr et al., J. Exp. Med. 175, 481-487, 1992.
Engelhard, V. H. Curr. Opinion in Immunol. 6:13-22, 1994.
Farnoud, M.R. et al. Int. J. Cancer 61:27-34, (1995).
Fetsch PA, et al, Cancer 90(4):252 (2000).
Gabler, U. et al. Heart 75:358-362, (1996).
Gileadi et al., Eur. J. Immunol. 29:2213-2222, 1999.
Gold and Freedman, J. Exp. Med. 121: 439-462, (1965).
Guo et al., Nature, 360:364-366, 1992.
Gure et al. Int. J. Cancer. 72:965-971 (1997).
Heikenwalder et al., "Lymphoid Follicle Destruction and Immunosuppression After Repeated CpG Oligodeoxynucleotide Administration," Nat Med. 10(2):187-92, 2004.
Hemmi, H. et al., Nat Immunol 3: 196-200, 2002.
International Search Report and the Written Opinion of the International Searching Authority, or the Declaration dated Dec. 4, 2006 for PCT/US2006/023498.
International Search Report and Written Opinion of the International Searching Authority dated Aug. 8, 2006 from International Application No. PCT/US2005/047250.
International Search Report for International Application No. PCT/US2004/019546, date of mailing Jun. 8, 2005.
Jäger et al. J. Exp. Med. 187(2):265-270 (1998).
Kaczmarek, J. et al. Int. J. Cancer 59:11-16, (1994).
Karelina, T.V. and A.Z. Eisen Cancer Detect. Prey. 22:438-444, (1998).
Kessler et al., "Efficient Identification of Novel HLA-A (*)0201-presented cytotoxic T lymphocyte epitopes in the widely expressed tumor antigen PRAME by proteasome-mediated digestion analysis," Journal of Experimental Medicine, vol. 193, No. 1, pp. 73-88, Jan. 1, 2001.
Loridon-Rosa, B. et al. Cancer Res.50:1608-1612, (1990).
Mandel, U. et al. APMIS 102:695-702, (1994).
Marciani, D.J. "Vaccine adjuvants: role and mechanisms of action in vaccine immunogenicity." Drug Discovery Today. 8: 934-943 (2003).
Marciani, D.J. Drug Discovery Today 8:934-943, (2003).
Matsuura, H. and S. Hakomori Proc. Natl. Acad. Sci. USA 82:6517-6521, (1985).
Midulla, M. Cancer Res. 60:164-169, (2000).
Mincheff, M. et al. "Naked DNA and Adenoviral Immunizations for Immunotherapy of Prostate Cancer: A Phase I/II Clinical Trial," European Urology, 38(2): 208-217 (2000).
Mocellin S, et al., Exp Cell Res. Oct. 1, 2004;299(2):267-78.
Morel et al., Immunity 12:107-117, 2000.
Neri, D. et al. Nat. Biotech. 15:1271-1275, (1997).
Neumann E et al, Cancer Res. 58:4090 (1998).
Nicolo, G. et al. Cell Differ. Dev. 32:401-408, (1990).
Okano F, et al. J Immunol. Mar. 1, 2005;174(5):2645-52.
Online Mendelian Inheritance in Man, record No. 114890.
Online Mendelian Inheritance in Man, record No. 164870.
Oyama, F. et al. Cancer Res. 53:2005-2011, (1993).
Parker et al. J. Immunol. 152:163-175 (1994).
Parkhurst et al. J. Immunol. 157(6):2539-2548 (1996).
Partial European Search Report for Application No. EP 02 72 3804 dated Nov. 2, 2004.
Pascolo, et al. "HLA-A2.1-restricted Education and Cytolytic Activity of CD8+ T Lymphocytes from β2 Microglobulin (β2m) HLA-A2.1 Monochain Transgenic H-2D$^b$β2m Double Knockout Mice." J. Exp. Med. 185(12): 2043-51 (1997).
Perkins et al., J. Immunology, 146(7):2137-2144, 1991.
Probst-Kepper et al. J. Immunol. 173:5610-5616 (2004).
Pujuguet, P. et al. Am. J. Pathol. 148:579-592, (1996).
Rammensee et al. MHC Ligands and Peptide Motifs. New York: Landes Bioscience, 1997.
Regner et al. Exp. Clin. Immunogenet. 13(1):30-35 (1996).
Remington: The Science and Practice of Pharmacy, (Nineteenth Edition; Chapters 86-88 1995).
Renkvist, N. et al., "A listing of tumor antigens recognized by T cells," Cancer Immunology Immunotherapy, 50:3-15 (2001).
Safran H et al, Am J Clin Oncol. 24:496 (2001).
Sahin, U et al, Clin Cancer Res. 6:3916 (2000).
Salgaller et al. Cancer Res. 55:4972-4979 (1995).

Sasada et al. *Eur. J. Immunol.* 30:1281-1289 (2000).
Scanlan MJ et al, Cancer lett 150:155 (2000).
Scanlan, et al. "The cancer/testis genes: Review, standardization, and commentary." *Cancer Immunity.* 4: 1-15 (Jan. 23, 2004).
Schönbach et al. *Nucleic Acids Research.* 28(1):222-224 (2000).
Schönbach et al. *Nucleic Acids Research.* 30(1):226-229 (2002).
Schultz-Thater E et al, Br J Cancer 83:204 (2000).
Selvaggi G et al, Cancer 94:2669 (2002).
Shastri et al., J. Immunology, 155:4339-4346, 1995.
Sizemore, D.R. et al., Science 270:299-302, (1995).
Slamon, et al., New Eng. J. Med. 344:783-792, (2001).
Stauss et al. *Proc. Natl. Acad. Sci. USA.* 89:7871-7875 (1992).
Supplementary European Search Report for Application No. EP 02 72 3804 dated Jan. 2, 2005.
Tarli, et al., Blood 94(1):192-98 (1999).
Theobald et al., J. Exp. Med., 188(6)1017-1028, 1998.
Tsai et al. *J. Immunol.* 158:1796-1802 (1997).
Tureci, O., et al. Proc. Natl. Acad. Sci. USA 95:5211-5216, (1998).
URL: http:www.cancerimmunity.org/SEREX/.
Valmori et al. *J Immunol.* 160(4): 1750-1758 (1998).
van de Vijver, et al., New Eng. J. Med. 319:1239-1245, (1988).
Van den Eynde, B., et al., J. Exp. Med. 182: 689-698, (1995).
Van Mierlo, et al. "Activation of Dendritic Cells that Cross-Present Tumor-Derived Antigen Licenses CD8+ CTL to Cause Tumor Eradication." The Journal of Immunology. 173: 6753-6759 (2004).
Velculiscu V.E. et al., Nat. Genet. 23:387-388, (1999).
Vertuani et al. *J Immunol.* 172(6): 3501-3508 (2004).
Von Boehmer et al., "The Manipulation of Immunity," *EMBO Reports*, vol. 5, No. 8, 2004.
Wagner et al. *Cancer Immunity.* 3:18 (2003).
Wang et al., Cellular Immunology, 143:284-297, 1992.
Weber R.W., "Adverse Reactions to Biological Modifiers," *Curr Opin Allergy Clin Immunol.* 4:277-83 2004.
World Wide Web page of Hans-Georg Rammensee, Jutta Bachmann, Niels Emmerich, Stefan Stevanovic: SYFPEITHI: An Internet Database for MHC Ligands and Peptide Motifs (hypertext transfer protocol access via: syfpeithi. bmi-heidelberg. com/ scripts/ MHCServer. dll/ home.htm) and "bimas. dcrt. nih. gov/ molbio/ hla_bind."
Yang, et al. "Persistent Toll-like receptor signals are required for reversal of regulatory T cell-mediated CD8 tolerance." Nature Immunology. 5(5): 508-515 (2004).
Zhang et al. *J. Mol. Biol.* 281:929-947 (1998).

* cited by examiner

*Plasmid Design*

MKRPSIKR-*SLLQHLIGL*-
ALQSLLQHLIGLSNLTHVLYPVPLESYEDIHGTLHLERLAYLHARLRELLCELGRP
SMVWLSANPCPHCGDRTFYDPEPILCPCFMPNKL**NLLHETDSAVATARRPRW
LCAGALVLAGGFFLLGFLFGWFIK***SAQLAGAKGVILYSDPADYFAPGVKSYPDGW
NLPGGGVQRGNILNLNGAGDPLTPGYPANEYAYRRGIAEAV***GLPSIPVHPI*-RK-
GLPSIPVHPI-LV-GLPSIPVHPI-KRISPEKEEQYIAKR-GLPSIPVHPI-KRPSIK-
RGLPSIPVHPV

FIG. 8

MNLLHETDSAVATARRPRWLCAGALVLAGGFFLLGFLFGWFIKSA*QLAGAKGVILYSDPADY
FAPGVKSYPDGWNLPGGGVQRGNILNLNGAGDPLTPGYPANEYAYRRGIAEAV***GLPS
IPVHPI***ALQSLLQHLIGLSNLTHVLYPVPLESYEDIHGTLHLERLAYLHARLRELLC
ELGRPSMVWLSANPCPHCGDRTFYDPEPILCPCFMPN-KR-SLLQHLIGL-
GDAAY-SLLQHLIGL-ISPEKEEQYIA-SLLQHLIGL-KRPSIKR-GLPSIPVHPV

FIG. 9

METHODS AND COMPOSITIONS TO ELICIT MULTIVALENT IMMUNE RESPONSES AGAINST DOMINANT AND SUBDOMINANT EPITOPES, EXPRESSED ON CANCER CELLS AND TUMOR STROMA

The present application claims the benefit of the filing date of U.S. Provisional Patent Application Ser. No. 60/691,579, filed on Jun. 17, 2005, the entirety of which is incorporated herein by reference without disclaimer.

BACKGROUND OF THE INVENTION

1. Field of the Invention

The invention disclosed herein is directed to inducing an MHC class-I restricted immune response and controlling the nature and magnitude of the response, thereby promoting effective immunologic intervention in pathogenic processes. The invention relates to immunogenic compositions that can stimulate a cellular immune response against a target cell. Disclosed herein is an immunogenic composition comprising a nucleic acid construct encoding the CTL epitopes $PRAME_{425\text{-}433}$ and $PSMA_{288\text{-}297}$ or a cross-reactive analogue of either or both of epitopes. The invention also provides methods of using the described immunogenic composition to elicit a balanced immune response in a subject to whom such compositions are administered.

2. Description of the Related Art

Cancer generally develops when cells in a part of the body continue to grow and divide in an unorderly manner unlike normal cells that grow, divide, and die in an orderly fashion. Although there are many kinds of cancer, they usually start because of out-of-control growth of abnormal cells.

Usual treatment options for cancer include surgery, radiation therapy, and chemotherapy. A fourth branch of treatment is developing, which is referred to as immunotherapy. Immunotherapies attempt to help the immune system recognize cancer cells, and/or to strengthen a response against cancer cells in order to destroy the cancer. Immunotherapies include active and passive immunotherapies. Active immunotherapies attempt to stimulate the body's own immune system to fight the disease. Passive immunotherapies generally do not rely on the body to attack the disease; instead, they use immune system components (such as antibodies) created outside of the patient's body.

Despite various types of cancer treatments, a continuing need exists for additional treatment options. Manipulation of the immune system by use of an anticancer vaccine is one such approach.

To generate a vaccine or other immunogenic composition, an antigen or epitope against which an immune response can be mounted is introduced to a subject. Although neoplastic (cancer) cells are derived from and therefore are substantially identical to normal cells on a genetic level, many neoplastic cells are known to present tumor-associated antigens (Tu-AAs). In theory, these antigens could be used by a subject's immune system to recognize and attack the neoplastic cells as foreign. Unfortunately, neoplastic cells generally appear to be ignored by the host's immune system.

The immune system can be categorized into two discrete effector arms. The first is innate immunity, which involves numerous cellular components and soluble factors that respond to all infectious challenges. The other is the adaptive immune response, which is customized to respond specifically to precise epitopes from infectious agents. The adaptive immune response is further broken down into two effector arms known as the humoral and cellular immune systems. The humoral arm is centered on the production of antibodies by B-lymphocytes while the cellular arm involves the killer cell activity of cytotoxic T lymphocytes.

Cytotoxic T lymphocytes (CTL) do not recognize epitopes on the infectious agents themselves. Rather, CTL detect fragments of antigens derived from infectious agents that are displayed on the surface of infected cells. As a result antigens are visible to CTL only after they have been processed by the infected cell and thus displayed on the surface of the cell.

The antigen processing and display system on the surface of cells has been well established. CTL recognize short peptide antigens, which are displayed on the surface in non-covalent association with class I major histocompatibility complex molecules (MHC). These class I peptides are in turn derived from the degradation of cytosolic proteins.

In most instances, neoplastic processes evolve to avoid the immune defense mechanisms by employing a range of strategies that result in immune ignorance, tolerance or deviation. Methods that effectively break immune tolerance or repair immune deviation against antigens expressed on cancer cells have been described in the literature (Okano F, et al. *J Immunol.* 2005, Mar 1;174(5):2645-52; Mocellin S, et al., *Exp Cell Res.* 2004 Oct 1;299(2);267-78; Banat G A, et al., *Cancer Immunol Immunother.* 2001 Jan;49(11):573-86) and despite their association with significant levels of systemic immunity, rarely result in reduction of tumor burden. Significant limiting factors impacting this process are sub-optimal trafficking, local activation and/or activity of anti-tumoral effector cells. In fact, it has been shown in most instances that the intratumoral presence of immune cells is a rare occurrence—compared to that associated with inflammatory processes such as organ rejection, infections or autoimmune syndromes.

The immune response resulting from exposure to antigens (in a natural context or upon vaccination) that encompass multiple epitopes is inherently associated with a hierarchy relative to the magnitude of the immune response against different, individual epitopes. This occurs in the case of T cell epitopes such as MHC class I and class II restricted epitopes, where dominance and subdominance has been well documented. Dominant epitopes are those that elicit prominent and specific expansions of T cells; whereas subdominant epitopes elicit relatively reduced responses characterized by a limited expansion of specific T cells with diminished functionality.

There are multiple reasons for an immune response to focus on a subset of epitopes within an antigen, regardless of whether the antigen is natural or engineered. These reasons include but are not limited to the following: efficacy of generation of certain peptides or polypeptide precursors within proteasomes (for class I restricted) or endosomes (for class II restricted); their selective transport via TAP (for class I peptides) and alternative mechanisms to compartments where loading onto MHC occurs; their affinity for MHC molecules relative to chaperones or the invariant polypeptide chain that occupies the peptide-binding cleft of nascent MHC molecules and relative to other competing peptides resulting from processing of the same or alternative substrates; the stability of the resulting MHC-peptide complex; and the functionality of T cell repertoire.

In addition, two or more epitopes from different antigens brought together on the same artificial molecule assume a dominant/subdominant relationship due to their intrinsic properties (such as those described above). This limits the practical applicability of composite molecules for the purpose of immunotherapy, particularly when co-targeting of cancer cells (neoplastic) and stromal elements (such as neovasculature) is pursued.

SUMMARY OF THE INVENTION

To amplify immune mediated control of tumoral processes, embodiments of the present invention provide immune mediated attack of neovasculature, in addition to direct attack on tumor cells, as a component of a bi- or multi-valent vaccine strategy aimed at establishing an inflammatory environment within the tumor resulting in shrinkage, stabilization or diminution of growth rate and invasion (local or systemic). This methodology can be more effective in controlling tumor processes than strategies that target either cancer cells or the neovasculature alone and has beneficial implications in regard to therapeutic index (efficacy/safety).

Some embodiments relate to methods and compositions that modulate the immune responses against epitopes with different intrinsic immune properties (e.g. dominant versus subdominant status in a given immunization context), in a manner consistent with increasing the relative activity of subdominant epitopes to achieve co-induction of balanced immune responses against multiple epitopes. This invention is useful when co-targeting multiple antigens such as those expressed by cancer cells and/or underlying stroma.

In some embodiments, co-targeting of tumor neovasculature and cancerous cells, or of multiple antigens on cancer cells, can be achieved by immunotherapeutic compositions comprising expression vectors such as plasmids that elicit immunity against transformed cells, tumor cells and endothelial cells of the neovasculature. Design of plasmids in a "string of beads" format is accomplished as disclosed in U.S. Patent Publication Application No. 20030228634, entitled "EXPRESSION VECTORS ENCODING EPITOPES OF TARGET-ASSOCIATED ANTIGENS AND METHODS FOR THEIR DESIGN" and herein incorporated by reference in its entirety. A preferred embodiment is a bivalent plasmid comprising immunogenic elements derived from molecule(s) expressed on cancer cells and molecule(s) expressed on neovasculature. In particular embodiments of the invention, such molecules correspond to the PRAME and PSMA epitopes and cross-reactive analogues thereof.

In another embodiment, vectors such as plasmids express immunogenic elements derived from molecules co-expressed by cancer cells and neovasculature. In yet another embodiment, vectors such as plasmids express immunogenic elements derived from a receptor and its ligand, where either the receptor or ligand is expressed by the neovasculature, and cancer cells express the other.

In still another embodiment, vectors encode immunogenic components from molecules expressed by cancer cells or neovasculature (or other stromal cells) along with biological response modifiers, including modifiers that act via antigen receptors on B and T cells and those that do not.

In some embodiments, vectors can be administered in a chronological sequence with other immunogenic agents—such as peptides—for the purpose of amplifying or modulating the therapeutic activity against cancer cells, neovasculature or both (disclosed in U.S. Patent Application Publication No. 20050079152 entitled "METHODS TO CONTROL MHC CLASS I-RESTRICTED IMMUNE RESPONSE"; U.S. Provisional Patent Application No. 60/640,402, filed Dec. 29, 2004, and U.S. Publication No. 20060165711, all entitled METHODS TO ELICIT, ENHANCE, AND SUSTAIN IMMUNE RESPONSE AGAINST MHC CLASS I-RESTRICTED EPITOPES, FOR PROPHYLACTIC OR THERAPEUTIC PURPOSES; and U.S. Provisional Application No. 60/691,581 filed on Jun. 17, 2004, entitled MULTIVALENT IMMUNOTHERAPEUTICS FOR CARCINOMA, and U.S. patent application Ser. No. 11/455,279, entitled MUTLIVALENT IMMUNOTHERAPIES FOR CARCINOMA, filed on date even with this application both entitled, each of which is herein incorporated by reference in its entirety) and balancing the response against subdominant and dominant epitopes.

Inducing immune responses to epitopes that are "subdominant" in context of a native antigen provides benefit in treating cancer since such epitopes can be involved in negative selection (central or peripheral) occurring in diseased individuals. Thus, constructs encompassing multiple copies of a subdominant epitope can be used to induce an increased response against such an epitope while preserving immunity against dominant ones.

In addition, effective co-induction of immune responses against epitopes from different antigens presented by the same molecule can offer a more practical approach to generate immunity against multiple antigens. This has direct implications for treatment and prevention of tumoral and infectious diseases.

Overall, broader immune responses achieved by such methods and compositions are more effective in dealing with pathogenic processes as opposed to immune responses heavily dominated by a limited number of specificities. In addition, practicality of multivalent vectors in such methods and compositions can alleviate the need to use numerous components and cumbersome administration protocols to achieve balanced, multivalent responses.

Some embodiments relate to bivalent plasmids expressing PRAME and PSMA epitope sequences (such as those disclosed in the U.S. Patent Application Publication Nos. 20030220239, 20050221440, 20050142144 and PCT Patent Publication No. PCT/US/11101 entitled "EPITOPE SEQUENCES" herein each incorporated by reference in its entirety) and methods of use of these compositions, individually or in combination with other plasmids, to elicit a balanced immune response. Such methods can include an initiating or entraining step wherein the composition can be delivered to various locations on the animal, but preferably is delivered to the lymphatic system, for example a lymph node. The entrainment step can include one or more deliveries of that composition, for example, spread out over a period of time or in a continuous fashion over a period of time.

The methods can further include an amplification step comprising administering a composition comprising a peptide immunogen, having substantial similarity or functional similarity to the corresponding epitopes encoded by the nucleic acid composition. For example, the immunogen can be a cross reactive sequence of the corresponding epitope. The amplification step can be performed one or more times, for example, at intervals over a period of time, in one bolus, or continuously over a period of time. Although not required in all embodiments, some embodiments can include the use of compositions that include an immunopotentiator or adjuvant.

It has been observed that by using this type of immunization protocol that not only can the plasmid initiate an immune response, it biases the response and its subsequent amplification toward an effector as opposed to a regulatory character. Without this prior nucleic acid-based immunization, the repeated administration of peptide leads to a response ever more dominated by regulatory T cells. The long-lived bias toward an effector response is termed entrainment.

Further embodiments include those in which the disclosed plasmids are used individually or in any combination. The peptide compositions corresponding to these epitopes and used in the amplification portion of the immunization strategy can be native sequences or peptide analogs substantially similar or functionally similar to the native epitope sequence. The peptides can be incorporated into the amplification protocol individually or in combinations of 2, 3, or 4 of the immunogens. Reasons for using less than all peptide epitopes include but are not limited to the following: 1) sub-optimal expression of any of the antigens; 2) the patient does not express, or no longer expresses the corresponding antigen; 3) a less robust response is being generated to one or another of the epitopes, in which case such peptide(s) can be given in the absence of the others in order to obtain a more balanced response; and 4) a peptide can be discontinued if it is generating some sort of immunotoxicity.

Additional embodiments relate to methods of modulating the immune response by changing the relative number of immunogen epitopes within a nucleic acid composition. These embodiments can also encompass changing the intrinsic immunogenicity of the immunogen, for example, by encoding amino acid substitutions within the immunogen epitope.

Embodiments additionally can encompass methods of modulating the immune response by selective up-regulation by peptide boost. The peptide compositions corresponding to this amplification step can be native sequences or peptide analogs substantially similar or functionally similar to the native epitope sequence. The selective up-regulation can be achieved by administration of the peptide corresponding to the subdominant epitope in order to obtain a balanced immune response.

Still other embodiments include plasmids that encode an analogue of either the PSMA or PRAME epitopes. Further embodiments can include different epitopes (such as those disclosed in U.S. Patent Application Publication Nos. 20030220239 and 20040180354 both entitled "EPITOPE SEQUENCES" and herein incorporated by reference in their entirety) and analogues substituted in similar combination as the epitopes expressed in the RP8 and RP12 plasmids and corresponding peptide immunogens (such as those disclosed in U.S. Provisional Patent Application No. 60/691,889 entitled "EPITOPE ANALOGUES", filed on Jun. 17, 2005, and herein incorporated by reference in its entirety) administered as the amplification portion of the immunization strategy.

Some embodiments relate to nucleic acid constructs encoding a polypeptide that includes one or more copies of CTL epitope $PSMA_{288-297}$ (SEQ ID NO:6) and one or more copies of CTL epitope $PRAME_{425-433}$ (SEQ ID NO:5), or a cross-reactive analogue comprising 1-3 substitutions of one or both of the epitopes, wherein the polypeptide does not include a whole antigen. The one or both epitopes can be encoded within a liberation sequence, for example. The polypeptide further can include a sequence encoding one or more epitope clusters. The nucleic acid construct can include a PRAME epitope cluster, for example, amino acid 422-509 of PRAME (SEQ ID NO:21). The nucleic acid construct can include a PSMA epitope cluster, for example, one or more epitope clusters can be amino acids 3-45 (SEQ ID NO:22) or 217-297 of PSMA (SEQ ID NO:23). The PSMA epitope analogue can contain a I297V substitution, for example. The nucleic acid construct further can include one or more of a nuclear import sequence, a promoter (for example, a cytomegalovirus (CMV) promoter), a poly-A sequence, or one or more of a CpG immunostimulatory motifs. The liberation sequence of both the PRAME and PSMA epitopes can be located, for example, in the N-terminal portion of the encoded polypeptide. The encoded polypeptide can be, for example, SEQ ID NO:2. The liberation sequence of both the PRAME and PSMA epitopes can be located, for example, in the C-terminal portion of the encoded polypeptide. For example, the encoded polypeptide can be SEQ ID NO:4.

Some embodiments relate to immunogenic compositions that include a nucleic acid construct described above and elsewhere herein.

Some embodiments relate to methods of treating an individual having cancer, the methods can include the step of administering a therapeutically effective amount of a nucleic acid construct described above and elsewhere herein. The nucleic acid construct can be administered intranodally, for example. The individual can have a cancer that expresses PRAME (SEQ ID NO:20), PSMA (SEQ ID NO:19), or both in neoplastic cells or tumor-associated neovasculature cells.

Some embodiments relate to methods of treating an individual having cancer. The methods can include the steps of administering an effective amount of the nucleic acid construct described above and elsewhere herein to induce an immune response; and amplifying the immune response by boosting with at least one peptide analogue corresponding to an epitope encoded by the nucleic acid construct. The individual can have, for example, a cancer that expresses PRAME on cancer cells and PSMA on tumor-associated vasculature cells. The individual can have a cancer that expresses PRAME, PSMA, or both in neoplastic cells or tumor-associated neovasculature cells.

Some embodiments relate to use of an immunogenic composition or nucleic acid construct as described above and elsewhere herein in the preparation of a medicament for the treatment of an individual having cancer. The medicament can be for the treatment of an individual having cancer by administering the medicament intranodally. The individual can have a cancer that expresses PRAME, PSMA, or both in neoplastic cells or tumor-associated neovasculature cells.

Some embodiments relate to the use of an immunogenic composition or a nucleic acid construct as described above and elsewhere herein in the preparation of a medicament for use in the inducing an immune response targeting of tumor associated neovasculature. For example, the tumor-associated vasculature cells displays PRAME.

BRIEF DESCRIPTION OF THE DRAWINGS

FIG. 8. Polypeptide sequence for RP8 (SEQ ID NO:2).

FIG. 9. Polypeptide sequence for RP12 (SEQ ID NO:4).

DETAILED DESCRIPTION OF THE PREFERRED EMBODIMENT

Figure 1:
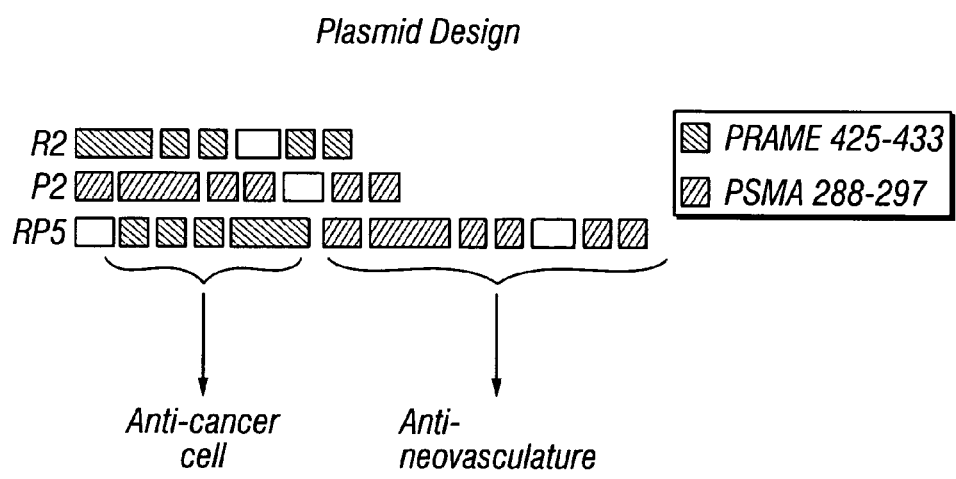
FIG. 1. Structure of two monovalent plasmids and one bivalent plasmid.

Embodiments relate to compositions that can elicit multivalent immune responses against dominant and subdominant epitopes. Some embodiments also relate to methods of designing the composition by: selecting antigens that are expressed by cancer cells and/or stromal (neovasculature) cells; defining epitopes that can have different intrinsic immune properties, that constitute valid immune targets on such cancer or stromal cells; and modulating the relative number of dominant and subdominant epitopes within a certain molecule (such as a therapeutic vector) by decreasing the ratio between the number of dominant and subdominant epitopes, while providing optimal flanking residues for appropriate generation within processing compartments.

Additional methods are described such as replacing one or multiple copies of subdominant epitopes with analogue sequences or preferentially positioning epitopes within the molecule to modify the relative immunogenicity of such epitopes and ensure a more balanced, multivalent response. Testing for efficacy can follow the design of a set of candidate epitopes. Use of such molecules can be complemented by selective amplification of responses against subdominant epitopes, in the context of prime-boost immunization strategies.

The general method for vaccine design can involve utilizing a defined algorithm that starts with a natural or artificial sequence to find the correct ratio of dominant and subdominant epitopes for plasmids, vectors, and molecules encompassing multiple copies of dominant and subdominant epitopes; engineering a set of compounds; in vitro and in vivo characterization steps; and selection of appropriate plasmids or other vectors eliciting the desired balanced immune response.

An epitope as referred to herein, is a molecule or substance capable of stimulating an immune response. In preferred embodiments, epitopes according to this definition include but are not necessarily limited to a polypeptide and a nucleic acid encoding a polypeptide, wherein the polypeptide is capable of stimulating an immune response. In other preferred embodiments, epitopes according to this definition include but are not necessarily limited to peptides presented on the surface of cells, the peptides being non-covalently bound to the binding cleft of class I MHC, such that they can interact with T cell receptors.

An MHC epitope as referred to herein is a polypeptide having a known or predicted binding affinity for a mammalian class I or class II major histocompatibility complex (MHC) molecule.

An immune epitope referred to herein, is a polypeptide fragment that is an MHC epitope, and that is displayed on a cell in which immune proteasomes are predominantly active. In another preferred embodiment, an immune epitope is defined as a polypeptide containing an immune epitope according to the foregoing definition, which is flanked by one to several additional amino acids. In another preferred embodiment, an immune epitope is defined as a polypeptide including an epitope cluster sequence, having at least two polypeptide sequences having a known or predicted affinity for a class I MHC. In yet another preferred embodiment, an immune epitope is defined as a nucleic acid that encodes an immune epitope according to any of the foregoing definitions.

SUBSTANTIAL SIMILARITY—this term is used to refer to sequences that differ from a reference sequence in an inconsequential way as judged by examination of the sequence. Nucleic acid sequences encoding the same amino acid sequence are substantially similar despite differences in degenerate positions or modest differences in length or composition of any non-coding regions. Amino acid sequences differing only by conservative substitution or minor length variations are substantially similar. Additionally, amino acid sequences comprising housekeeping epitopes that differ in the number of N-terminal flanking residues, or immune epitopes and epitope clusters that differ in the number of flanking residues at either terminus, are substantially similar. Nucleic acids that encode substantially similar amino acid sequences are themselves also substantially similar.

FUNCTIONAL SIMILARITY—this term is used to refer to sequences that differ from a reference sequence in an inconsequential way as judged by examination of a biological or biochemical property, although the sequences may not be substantially similar. For example, two nucleic acids can be useful as hybridization probes for the same sequence but encode differing amino acid sequences. Two peptides that induce cross-reactive CTL responses are functionally similar even if they differ by non-conservative amino acid substitutions (and thus do not meet the substantial similarity definition). Pairs of antibodies, or TCRs, that recognize the same epitope can be functionally similar to each other despite whatever structural differences exist. In testing for functional similarity of immunogenicity one would generally immunize with the "altered" antigen and test the ability of the elicited response (Ab, CTL, cytokine production, etc.) to recognize the target antigen. Accordingly, two sequences may be designed to differ in certain respects while retaining the same function. Such designed sequence variants are among the embodiments of the present invention.

I. Plasmid Construction

Some embodiments of the present invention provide a number of plasmids, e.g., pRP8 (SEQ ID NO:1), pRP9, pRP10, pRP11, pRP12 (SEQ ID NO:3), and pRP13, having the ability to elicit or promote a bivalent response against the tumor associated antigens PRAME and PSMA, specifically against the epitopes PRAME$_{425-433}$ (SEQ ID NO:5) and PSMA$_{288-297}$ (SEQ ID NO:6). In particular embodiments of the invention there are provided the plasmids, pRP12 and pRP8 as immunogenic compositions. The methodology for generating plasmid constructs of the invention are as detailed, below.

Plasmid construction in preferred embodiments can entail stepwise ligation of sets of long complementary oligonucleotides resulting in the generation of DNA sequence encoding epitopes arrayed as a "string-of-beads." These DNAs bear appropriate cohesive ends for restriction enzymes that can be used for further ligation with DNAs encoding epitope cluster regions, which are amplified by performing PCR on cloned cDNA for PSMA or PRAME as a template. The entire insert is then ligated into the vector backbone between Afl II and EcoR I restriction sites. The entire coding sequence is verified by DNA sequencing. PCR-based mutagenesis can be used to generate sequence encoding analogue epitope peptide, or to adjust the copies number of dominant/subdominant epitopes to achieve the desired ratio. The sequences of the two plasmids, RP8 and RP12, are described in detail and disclosed as SEQ ID NO.1 and SEQ ID NO.3. For the specific plasmids described herein, the vector backbone is a modified version of pVAX, by Invitrogen (Carlsbad, Calif.), which has been previously disclosed in U.S. Pat. No. 6,709,844 entitled Avoidance of Undesirable Replication Intermediates in Plasmid Propagation, and U.S. patent application Ser. No. 09/561,572 entitled Expression Vectors Encoding Epitopes of Target-Associated Antigens, each of which is hereby incorporated by reference in its entirety. One of skill in the art will recognize that the coding sequences of the present invention can be placed in any nucleic acid vector suitable for use as a vaccine without exceeding the scope of the invention. For example, the sequences encoding the other mentioned plasmids can be inserted into the same or a similar backbone as used in pRP8 and pRP12 plasmids.

pRP8 and pRP12 are recombinant DNA plasmids that encode one polypeptide with HLA A2-restricted CTL epitopes from PSMA (288-297) (SEQ ID NO:6) and an analogue thereof) and PRAME (425-433) (SEQ ID NO:5). Both polypeptides also include regions comprising epitope clusters of PSMA (3-45) (SEQ ID NO:22), (217-297) (SEQ ID NO:24) and PRAME (422-509) (SEQ ID NO:21). Flanking the defined PSMA and PRAME epitopes are short amino acid sequences optimal for liberation of the epitopes in question by immunoproteasome processing. The coding sequence for the polypeptide in the plasmid is under the control of promoter/enhancer sequence from cytomegalovirus (CMVp), which allows efficient transcription of mRNA for the polypeptide upon uptake by APCs. The bovine growth hormone polyadenylation signal (BGH polyA) at the 3' end of the encoding sequence provides a signal for polyadenylation of the messenger to increase its stability as well as for translocation out of the nucleus into the cytoplasm for translation. To facilitate plasmid transport into the nucleus after uptake, a nuclear import sequence (NIS) from simian virus 40 (SV40) has been inserted in the plasmid backbone. The plasmid carries two copies of a CpG immunostimulatory motif, one in the NIS sequence and one in the plasmid backbone. Lastly, two prokaryotic genetic elements in the plasmid are responsible for amplification in *E. coli*, the kanamycin resistance gene (Kan R) and the pMB1 bacterial origin of replication.

A. RP8 Recombinant DNA Plasmid

For RP8, the amino acid sequence of the encoded polypeptide (297 amino acid residues in length; SEQ ID NO:2) contains two liberation sequences, a 17 amino acid substrate at its N-terminus for $PRAME_{425\text{-}433}$ (MKRPSIKR-SLLQHLIGL; SEQ ID NO:25) and a 66 ammo acid substrate at its C-terminus for $PSMA_{288\text{-}297}$ (RK-GLPSIPVHPI-LV-GLPSIPVHPI-KRISPEKEEQYIAKR-GLPSIPVHPI-KRPSIK-RGLP-SIPVHPV; SEQ ID NO:8). The entire polypeptide sequence of the encoded immunogen (SEQ ID NO:2) is shown in FIG. 8.

The stretch of the first 8 amino acid residues is an artificial sequence that has been shown to facilitate processing of CTL epitopes by immunoproteasomes. The next 9 amino acids (in italics) are $PRAME_{425\text{-}433}$ (SEQ ID NO:5), a potent HLA A2-specific CTL epitope that triggers strong anti-tumor immune responses in both in vitro immunization of human PBMC and in vivo immunization in mice. This PRAME epitope sequence is followed by a segment (amino acid 18-105 of the immunogen) of $PRAME_{422\text{-}509}$, comprising two epitope clusters: $PRAME_{422\text{-}443}$ (SEQ ID NO:26) and $PRAME_{459\text{-}487}$ (SEQ ID NO:27). Two PSMA epitope clusters (in italics), $PSMA_{3\text{-}45}$ (SEQ ID NO:22) (amino acid 108-150;) and $PSMA_{217\text{-}297}$ (SEQ ID NO:24) (amino acid 151-231), are placed after the PRAME epitope cluster. These and other PRAME and PSMA epitope clusters have been disclosed in U.S. patent application Ser. Nos. 10/117,937, 11/067,064, and 11/067,159, each entitled Epitope Sequences and each of which is hereby incorporated by reference in its entirety. These epitope clusters contain a number of predicted HLA A2-specific epitopes and thus can be useful in generating a response to immune epitopes (described in U.S. Patent Application Publication No. 20030215425 entitled EPITOPE SYNCHRONIZATION IN ANTIGEN PRESENTING CELLS and U.S. Patent Application Publication Nos. 20030228634; 20040132088; and 20040203051, entitled EPITOPE CLUSTERS, each of which is hereby incorporated by reference in its entirety). A "string-of-beads" epitope array with multiple copies of $PSMA_{288\text{-}297}$ (GLP-SIPVHPI (SEQ ID NO:6); in boldface) constitutes the rest of the polypeptide (amino acid 232-297). Four copies of $PSMA_{288\text{-}297}$ are incorporated with the last copy being an analogue (GLPSIPVHPV; SEQ ID NO:7). Both the native $PSMA_{288\text{-}297}$ and its analogue have been shown to induce significant CTL responses in both in vitro immunization of human PBMC and in vivo immunization in mice with the analogue displaying elevated MHC class I binding and immunogenicity. Between $PSMA_{288\text{-}297}$ epitope sequences are short amino acid sequences designated to be "cleavage helper sequences" to facilitate the processing and liberation of the epitope. These two epitopes are thus encoded in such a manner that they can be expressed, processed, and presented by pAPCs.

B. RP12 Recombinant DNA Plasmid

For the RP12 plasmid, the amino acid sequence of the encoded polypeptide (275 amino acid residues in length; SEQ ID NO:4) contains one amino acid substrate or liberation sequence and a hybrid "string-of-beads" encompassing a substrate at its C-terminus for the liberation of both the PRAME and PSMA epitopes. The entire polypeptide sequence of the encoded immunogen is shown in FIG. 9. The liberation sequence represented as SEQ ID NO:9 is as follows: KR-SLLQHLIGL-GDAAY-SLLQHLIGL-ISPEKEEQYIA-SLLQHLIGL-KRPSIKR-GLPSIPVHPV.

Segments of amino acid 2-44, 45-126, and 127-213 of the encoded immunogen are epitope clusters joined one to the next: $PSMA_{3\text{-}45}$ (SEQ ID NO:22), $PSMA_{217\text{-}297}$ (SEQ ID NO:23), and $PRAME_{422\text{-}509}$ (SEQ ID NO:21), respectively. In the "string-of-beads" hybrid substrate, there are 3 copies of $PRAME_{425\text{-}433}$ (SLLQHLIGL; in boldface; SEQ ID NO:5) and one copy of $PSMA_{288\text{-}297}$ analogue (GLPSIPVHPV; in sans serif boldface; SEQ ID NO:7) at the C-terminus of the polypeptide. Between the $PRAME_{425\text{-}433}$ and $PSMA_{288\text{-}297}$ epitope sequences are the short amino acid sequences designated to be "cleavage helper sequences" to facilitate processing and liberation of the epitopes. These two epitopes are thus encoded in such a manner that they can be expressed, processed, and presented by pAPCs.

Figure 3:
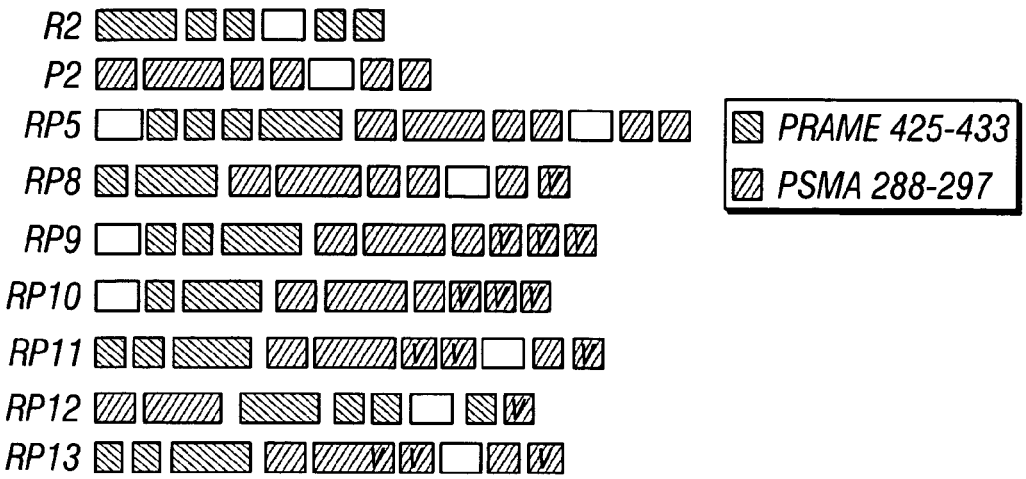
FIG. 3. Structure of additional plasmids designed expressing both PRAME and PSMA epitopes. Structure of the monovalent PRAME plasmid R2 is depicted. P2 represents the monovalent PSMA plasmid.

Further details on the RP12 plasmid are disclosed in U.S. Provisional Patent Application No. 60/691,579, filed on Jun. 17, 2005, entitled METHODS AND COMPOSITIONS TO ELICIT MULTIVALENT IMMUNE RESPONSES AGAINST DOMINANT AND SUBDOMINANT EPITOPES, EXPRESSED ON CANCER CELLS AND TUMOR STROMA, incorporated herein by reference in its entirety. All other plasmids were constructed in a similar fashion using the methodology as applied to RP8 and RP12. The plasmid R2, also referred to as pCTLR2, is disclosed in the Examples. The P2 plasmid as shown in FIGS. 1 and 3, is a monovalent PSMA plasmid. The RP5 plasmid encompasses elements from both P2 and R2.

Various methodologies for constructing or designing plasmids are well established in the art as would be known to the skilled artisan. Such methodologies are described in many references, such as, for example, Molecular Cloning, Sambrook J and Russell D. W., CSHL Press, (2001), specifically incorporated herein by reference.

In constructing the nucleic acids encoding the polypeptide epitopes of the invention, the gene sequence of the associated tumor associated antigen (e.g., PRAME and PSMA) can be used, or the polynucleotide can be assembled from any of the corresponding codons. For a 10 amino acid epitope this can constitute on the order of $10^6$ different sequences, depending on the particular amino acid composition. While large, this is a distinct and readily definable set representing a miniscule fraction of the $>10^{18}$ possible polynucleotides of this length, and thus in some embodiments, equivalents of a particular sequence disclosed herein encompass such distinct and readily definable variations on the listed sequence. In choosing a particular one of these sequences to use in a vaccine, considerations such as codon usage, self-complementarity, restriction sites, chemical stability, etc. can be used as will be apparent to one skilled in the art.

An epitope cluster as contemplated in the present invention is a polypeptide, or a nucleic acid sequence encoding it, that is a segment of a native protein sequence comprising two or more known or predicted epitopes with binding affinity for a shared MHC restriction element, wherein the density of epitopes within the cluster is greater than the density of all known or predicted epitopes with binding affinity for the shared MHC restriction element within the complete protein sequence. Epitope clusters and their uses are described in U.S. Patent Application Publication Nos. 20030220239, 20050221440, 20050142144; 20030215425, 20030228634, 20040132088, 20040203051 and PCT Patent Application Publication No. PCT/US/11101; all of which are incorporated herein by reference in their entirety.

A substrate or liberation sequence as employed in the present invention, is a designed or engineered sequence comprising or encoding a PRAME and/or PSMA epitope embedded in a larger sequence that provides a context allowing the PRAME and/or PSMA epitope to be liberated by immunoproteasomal processing, directly or in combination with N-terminal trimming or other processes.

The following are additional examples of encoded polypeptide sequences that can be used in some embodiments, for example, they can be encoded by the various plasmids or used in the methods, etc.

```
R2                                          (SEQ ID NO: 10)
MALQSLLQHLIGLSNLTHVLYPVPLESYEDIHGTLHLERLAYLHARLREL
LCELGRPSMVWLSANPCPHCGDRTFYDPEPILCPCFMPNKRSLLQHLIGL
GDAAYSLLQHLIGLISPEKEEQYIASLLQHLIGLKRPSIKRSLLQHLIGL

P2                                          (SEQ ID NO: 11)
MNLLHETDSAVATARRPRWLCAGALVLAGGFFLLGFLFGWFIKSAQLAGA
KGVILYSDPADYFAPGVKSYPDGWNLPGGGVQRGNILNLNGAGDPLTPGY
PANEYAYRRGIAEAVGLPSIPVHPIRKGLPSIPVHPILVGLPSIPVHPIK
RISPEKEEQYIAKRGLPSIPVHPIKRPSIKRGLPSIPVHPI

RP5                                         (SEQ ID NO: 12)
MISPEKEEQYIASLLQHLIGLKRSLLQHLIGLKRPSIKRSLLQHLIGLAL
QSLLQHLIGLSNLTHVLYPVPLESYEDIHGTLHLERLAYLHARLRELLCE
LGRPSMVWLSANPCPHCGDRTFYDPEPILCPCFMPNKLNLLHETDSAVAT
ARRPRWLCAGALVLAGGFFLLGFLFGWFIKSAQLAGAKGVILYSDPADYF
APGVKSYPDGWNLPGGGVQRGNILNLNGAGDPLTPGYPANEYAYRRGIAE
AVGLPSIPVHPIRKGLPSIPVHPILVGLPSIPVHPIKRISPEKEEQYIAK
RGLPSIPVHPIKRPSIKRGLPSIPVHPI

RP9                                         (SEQ ID NO: 14)
MISPEKEEQYIASLLQHLIGLKRPSIKRSLLQHLIGLALQSLLQHLIGLS
NLTHVLYPVPLESYEDIHGTLHLERLAYLHARLRELLCELGRPSMVWLSA
NPCPHCGDRTFYDPEPILCPCFMPNKLNLLHETDSAVATARRPRWLCAGA
LVLAGGFFLLGFLFGWFIKSAQLAGAKGVILYSDPADYFAPGVKSYPDGW
NLPGGGVQRGNILNLNGAGDPLTPGYPANEYAYRRGIAEAVGLPSIPVHP
IRKGLPSIPVHPILVGLPSIPVHPVKRGLPSIPVHPVKRPSVKRGLPSIP
VHPV

RP10                                        (SEQ ID NO: 15)
MISPEKEEQYIASLLQHLIGLALQSLLQHLIGLSNLTHVLYPVPLESYED
IHGTLHLERLAYLHARLRELLCELGRPSMVWLSANPCPHCGDRTFYDPEP
ILCPCFMPNKLNLLHETDSAVATARRPRWLCAGALVLAGGFFLLGFLFGW
FIKSAQLAGAKGVILYSDPADYFAPGVKSYPDGWNLPGGGVQRGNILNLN
GAGDPLTPGYPANEYAYRRGIAEAVGLPSIPVHPIRKGLPSIPVHPILVG
LPSIPVHPVKRGLPSIPVHPVKRPSVKRGLPSIPVHPV

RP11                                        (SEQ ID NO: 16)
MKRSLLQHLIGLKRPSIKRSLLQHLIGLALQSLLQHLIGLSNLTHVLYPV
PLESYEDIHGTLHLERLAYLHARLRELLCELGRPSMVWLSANPCPHCGDR
TFYDPEPILCPCFMPNKLNLLHETDSAVATARRPRWLCAGALVLAGGFFL
LGFLFGWFIKSAQLAGAKGVILYSDPADYFAPGVKSYPDGWNLPGGGVQR
GNILNLNGAGDPLTPGYPANEYAYRRGIAEAVGLPSIPVHPIRKGLPSIP
VHPVLVGLPSIPVHPVKRISPEKEEQYIAKRGLPSIPVHPIKRPSIKRGL
PSIPVHPV

RP13                                        (SEQ ID NO: 18)
MKRSLLQHLIGLKRPSIKRSLLQHLIGLALQSLLQHLIGLSNLTHVLYPV
PLESYEDIHGTLHLERLAYLHARLRELLCELGRPSMVWLSANPCPHCGDR
TFYDPEPILCPCFMPNKLNLLHETDSAVATARRPRWLCAGALVLAGGFFL
LGFLFGWFIKSAQLAGAKGVILYSDPADYFAPGVKSYPDGWNLPGGGVQR
GNILNLNGAGDPLTPGYPANEYAYRRGIAEAVGLPSIPVHPVLVGLPSIP
VHPVKRISPEKEEQYIAKRGLPSIPVHPIKRPSIKRGLPSIPVHPV
```

II. Immunogenic Compositions of the Present Invention

The present invention contemplates the use of multiple molecules expressed by cancer cells and by the neovasculature as therapeutic targets in the treatment of cancer by active immunotherapy. Such molecules include tumor-associated antigens (TuAAs) which are antigens expressed by the cancer cell itself or associated with non-cancerous components of the tumor, such as tumor-associated neovasculature or other stroma. Determination of TuAA expression profiles can help to match a patient's cancer condition or type with an appropriate immunotherapeutic agent or regimen. In particular embodiments, epitopes of the tumor associated antigens PRAME and PSMA are employed in designing bivalent plasmids that can elicit a strong immune response in a subject to whom such plasmid are administered as a cancer therapeutics. Cross-reactive analogues of PRAME and PSMA are also contemplated in the embodiments of the present invention.

The tumor associated antigen PRAME (SEQ ID NO:20), employed in the present invention, is also known as MAPE, DAGE, and OIP4. PRAME is known in the art as a cancer-testis (CT) antigen. However, unlike many CT antigens, such as: MAGE, GAGE and BAGE, it is expressed in acute myeloid leukemias. PRAME as a TuAA is disclosed in U.S. Pat. No. 5,830,753, incorporated herein by reference in its entirety. In preferred embodiments, the present invention provides epitopes of PRAME and analogues thereof.

Another TuAA employed in the present invention is the prostate-specific membrane antigen (PSMA) (SEQ ID NO:19). PSMA is found to be highly expressed in prostate cancer cells. However, PSMA expression is also noted in normal prostate epithelium and in the neovasculature of non-prostatic tumors. PSMA as an anti-neovasculature preparation is disclosed in U.S. Provisional Patent Application No. 60/274,063, and U.S. Patent Publication Application Nos. 20030046714 and 20050260234; each of which is incorporated herein by reference in its entirety. PSMA as a TuAA is described in U.S. Pat. No. 5,538,866 incorporated herein by reference in its entirety. In preferred embodiments, the present invention provides epitopes of PSMA and analogues thereof.

Cross-reactive analogue as used herein may refer to a peptide comprising 1-3 amino acid substitutions, and/or one amino acid deletion or addition as compared to the native peptide sequence that induces effector function (e.g., cytolysis or cytokine secretion) distinguishable from background, from a CTL reactive with the native peptide. In preferred embodiments effector function is at least 30, 50, 60, 70, or 80% of that induced by the native peptide.

In some embodiments of the present invention, peptides comprising the native sequence or analogues (cross-reactive) of PRAME and PSMA may also be administered as a peptide boost in combination with the plasmids of the invention. Native peptide sequences and peptide analogues of PRAME and PSMA, arc disclosed in U.S. Patent Application No. 20060057673 and U.S. Provisional Patent Application No. 60/691,889, each of which is hereby incorporated by reference in its entirety. The peptide analogues, PRAME$_{425-433}$ L426Nva, L433Nle (SEQ ID NO:30) and PSMA$_{288-297}$ I297V (SEQ ID NO:7) are described in U.S. Provisional Application No. 60/580,962; U.S. patent application Ser. No. 11/155,929; U.S. Provisional Application No. 60/581,001; U.S. patent application Ser. No. 11/156,253; U.S. patent application Ser. No. 11/156,369 U.S. Provisional Patent Application No. 60/691,889, U.S. patent application Ser. No. 11/455,278, entitled PRAME PEPTIDE ANALOGUES, U.S. patent application Ser. No. 11/454,633, entitled PSMA PEPTIDE ANALOGUES, and U.S. patent application Ser. No. 11/454,300, entitled MELANOMA ANTIGEN PETIDE ANALOGUES each of which is hereby incorporated by reference in its entirety.

As discussed above, some embodiments relate to immunogenic compositions for the treatment of cancer comprising plasmids encoding CTL epitopes of PRAME and PSMA and cross-reactive analogues thereof. Such an immunogenic composition can elicit a robust or strong cell-mediated immune response to target a particular cancer thereby eliminating, eradicating or ameliorating the cancer in a subject.

III. Entraining-and-Amplifying Therapeutics for Administration

In a preferred embodiment, the present invention provides an immunogenic composition comprising a nucleic acid construct encoding the CTL epitopes PRAME$_{425-433}$ (SEQ ID NO:5) and PSMA$_{288-297}$ (SEQ ID NO:6) or a cross-reactive analogue of either or both these epitopes. In some embodiments of the invention a plasmid prime/peptide boost approach may be employed wherein the recombinant DNA plasmid expressing the PRAME and PSMA epitopes may be administered in conjunction with a synthetic peptides such as a PRAME and or PSMA peptide or analogue thereof.

The immunogenic composition of the invention comprising a nucleic acid construct encoding the CTL epitopes PRAME$_{425-433}$ and PSMA$_{288-297}$ or a cross-reactive analogue of one or both epitopes, can be delivered via lymph node injection, directly into the organs where the immune responses are initiated and amplified, according to an optimized immunization schedule. Embodiments of the current invention can be administered to patients with tumor tissue that express HLA-A2, particularly HLA-A*0201. Therefore, the immunogenic composition comprising a plasmid and one or more peptides or analogues thereof can be administered in treating a cancer in a subject. The disclosed embodiments of the present invention relate to entrain-and-amplify therapeutics for cancer that can be used to achieve a bi- or multivalent attack, offering the advantage of increasing the sensitivity of the tumor to attack.

Therefore, in particular embodiments, the present invention provides bivalent entraining-and-amplifying therapeutics for the treatment of cancer. Such bivalent therapeutics can target more than one antigen on a tumor cell. In instances where more than a single antigen on a tumor cell is targeted, the effective concentration of antitumor therapeutic is increased accordingly. Attack on stroma associated with the tumor, such as vasculature, can increase the accessibility of the tumor cells to the agent(s) targeting them. Thus, even an antigen that is also expressed on some normal tissue can receive greater consideration as a target antigen if the other antigens to be targeted in a bi- or multivalent attack are not also expressed by that tissue. The plasmids of the current invention can be used in conjunction with additional plasmids that express other epitopes, and corresponding amplifying peptides, to create therapeutic protocols of higher valency. Exemplary immunogenic products are disclosed in U.S. Provisional Patent Application No. 60/691,581, filed on Jun. 17, 2005 and U.S. patent application Ser. No. 11/455,279, filed on date even with the instant application, each entitled MULTIVALENT ENTRAIN-AND-AMPLIFY IMMUNOTHERAPEUTICS FOR CARCINOMA, and each incorporated by reference in its entirety.

An "entraining" immunogen as contemplated in the present invention includes in many embodiments an induction that confers particular stability on the immune profile of the induced lineage of T cells.

As contemplated in the present invention, the term "amplifying or amplification", as of a T cell response, includes in many embodiments a process for increasing the number of cells, the number of activated cells, the level of activity, rate of proliferation, or similar parameter of T cells involved in a specific response.

The entrain-and-amplify protocol employed in the present invention is described in greater detail in U.S. Patent Publication No. 20050079152, U.S. Provisional Patent Application No. 60/640,402, and U.S. patent application Ser. No. 11/323,572 each entitled "METHODS TO ELICIT, ENHANCE AND SUSTAIN IMMUNE RESPONSES AGAINST MHC CLASS I-RESTRICTED EPITOPES, FOR PROPHYLACTIC OR THERAPEUTIC PURPOSES" which are incorporated herein by reference in their entirety.

IV. Biological Response Modifiers (BRMs) or Immunopotentiators

In some embodiments, the present invention may further employ a biological response modifier (BRM) or immunopotentiator in conjunction with the immunogenic compositions comprising a recombinant DNA plasmid encoding the CTL epitopes PRAME and PSMA, in eliciting an immune response. The immunopotentiators or BRMs contemplated by the present invention can act in an immunosuppressive or immunostimulatory manner to mediate an immune response. Immunopotentiators or BRMs of the present invention may refer to any molecule that modulates the activity of the immune system, or the cells thereof, through an interaction other than with an antigen receptor. BRMs as contemplated in the present invention may further include natural or synthetic small organic molecules that exert immune modulating effects by stimulating pathways of innate immunity.

In particular embodiments, the present invention also contemplates immunopotentiators or BRMS which may include, but are not limited to, for example: cytokines such as IL-12, IL-18, GM-CSF, flt3 ligand (flt3L), interferons, TNF-alpha, and the like; chemokines such as IL-8, MIP-3alpha, MIP-1alpha, MCP-1, MCP-3, RANTES, and the like. Other examples of BRMs that may be utilized in the present invention are molecules that trigger cytokine or chemokine production, such as ligands for Toll-like receptors (TLRs), peptidoglycans, LPS or analogues, unmethylated CpG oligodeoxynuelotides (CpG ODNs); dsRNAs such as bacterial dsDNA (which contains CpG motifs) and synthetic dsRNA (polyI:C) APC and innate immune cells that bind to TLR9 and TLR3, respectively. One class of BRM includes mostly small organic natural or synthetic molecules, which exert immune modulating effects by stimulating pathways of innate immunity. Thus, small molecules that bind to TLRs such as a new generation of purely synthetic anti-viral imidazoquinolines, e.g., imiquimod and resiquimod, that have been found to stimulate the cellular path of immunity by binding the TLRs 7 and 8 (Hemmi, H. et al., *Nat Immunol* 3: 196-200, 2002; Dummer, R. et al., *Dermatology* 207: 116-118, 2003; each of which is incorporated herein by reference in its entirety) may be employed. BRMs may further include immunopotentiating adjuvants that activate pAPC or T cells including, for example: endocytic-Pattern Recognition Receptor (PRR) ligands, quillaja saponins, tucaresol and the like.

V. Methods of Delivering Compositions of the Present Invention

In the present invention, the preferred administration of the immunogenic composition comprising recombinant DNA plasmids encoding the CTL epitopes PRAME and PSMA, or such plasmids followed by one or more peptide(s) as one or more boost, is via lymph node injection. Other immunization protocols, for example, using plasmid for other than the initiation dose(s), relying on plasmid alone, or utilizing other types of boosting reagents, while less preferred embodiments, are not excluded from the scope of the invention. Embodiments of the present invention encompass bivalent plasmids expressing both of the immunogens PRAME and PSMA. In delivering the immunogenic compositions of the invention to a subject in need thereof, lymph node injection is preferred as it allows for delivery directly into the organs where the immune responses are initiated and amplified according to an optimized immunization schedule.

To introduce the immunogenic composition into the lymphatic system of the patient the composition is preferably directed to a lymph vessel, lymph node, the spleen, or other appropriate portion of the lymphatic system. In some embodiments each component is administered as a bolus. In other embodiments, one or more components are delivered by infusion, generally over several hours to several days. Preferably, the composition is directed to a lymph node such as an inguinal or axillary node by inserting a catheter or needle to the node and maintaining the catheter or needle throughout the delivery. Suitable needles or catheters are available made of metal or plastic (e.g., polyurethane, polyvinyl chloride (PVC), TEFLON, polyethylene, and the like). In inserting the catheter or needle into the inguinal node for example, the inguinal node is punctured under ultrasonographic control using a Vialon™ Insyte W™ cannula and catheter of 24G3/4 (Becton Dickinson, USA) which is fixed using Tegaderm™ transparent dressing (Tegaderm™, St. Paul, Minn., USA). An experienced radiologist generally does this procedure. The location of the catheter tip inside the inguinal lymph node is confirmed by injection of a minimal volume of saline, which immediately and visibly increases the size of the lymph node. The latter procedure allows confirmation that the tip is inside the node. This procedure can be performed to ensure that the tip does not slip out of the lymph node and can be repeated on various days after implantation of the catheter.

The therapeutic composition(s) of the present invention may be administered to a patient in a manner consistent with standard vaccine delivery protocols that are well known to one of ordinary skill in the art. Methods of administering immunogenic compositions of the present invention comprising plasmids and peptides or peptide analogues of the TuAAs PRAME and PSMA include, without limitation, transdermal, intranodal, perinodal, oral, intravenous, intradermal, intramuscular, intraperitoneal, and mucosal administration, delivery by injection or instillation or inhalation. A particularly useful method of vaccine delivery to elicit a CTL response is disclosed in Australian Patent No. 739189; U.S. Pat. Nos. 6,994,851 and 6,977,074 both entitled "A METHOD OF INDUCING A CTL RESPONSE".

Various parameters can be taken into account in delivering or administering an immunogenic composition to a subject. In addition, a dosage regimen and immunization schedule may be employed. Generally the amount of the components in the therapeutic composition will vary from patient to patient and from antigen to antigen, depending on such factors as: the activity of the antigen in inducing a response; the flow rate of the lymph through the patient's system; the weight and age of the subject; the type of disease and/or condition being treated; the severity of the disease or condition; previous or concurrent therapeutic interventions; the capacity of the individual's immune system to synthesize antibodies; the degree of protection desired; the manner of administration and the like, all of which can be readily determined by the practitioner.

In general the therapeutic composition may be delivered at a rate of from about 1 to about 500 microliters/hour or about 24 to about 12000 microliters/day. The concentration of the antigen is such that about 0.1 micrograms to about 10,000 micrograms of the antigen will be delivered during 24 hours. The flow rate is based on the knowledge that each minute approximately about 100 to about 1000 microliters of lymph fluid flows through an adult inguinal lymph node. The objective is to maximize local concentration of vaccine formulation in the lymph system. A certain amount of empirical investigation on patients will be necessary to determine the most efficacious level of infusion for a given vaccine preparation in humans.

In particular embodiments, the immunogenic composition of the present invention may be administered as a number of sequential doses. Such doses may be 2, 3, 4, or more doses as is needed to obtain the appropriate immune response. In further embodiments of the present invention, it is contemplated that the doses of the immunogenic composition would be administered within about seconds or minutes of each other into the right or left inguinal lymph nodes. For example, the plasmid (prime) may first be injected into the right lymph node followed within seconds or minutes by a second plasmid into the right or left inguinal lymph nodes. In other instances the combination of one or more plasmid expressing one or more immunogens may be administered. It is preferred that the subsequent injection following the first injection into the lymph node be within at about 1, 2, 3, 4, 5, 6 7, 8, 9, 10 or more minutes but not greater than about 30, 40, 50, or 60 minutes of the first injection. Similar considerations apply to the administration of two peptides individually to the right and left lymph nodes. It may be desirable to administer the doses of the immunogenic composition of the invention at an interval of days, where several days (1, 2, 3, 4, 5, 6, or 7, or more days) lapse between subsequent administrations. In other instances it may be desirable for subsequent administration(s) of the compositions of the invention to be administered via bilateral inguinal lymph node injection within about 1, 2, 3, or more weeks or within about 1, 2, 3, or more months following the initial dose administration.

Administration may be in any manner compatible with the dosage formulation and in such amount as will be therapeutically effective. An effective amount or dose of an immunogenic composition of the present invention is that amount needed to provide a desired response in the subject to be treated.

In addition to those already disclosed in this application, the following applications are hereby expressly incorporated by reference in their entireties. Useful methods for using the disclosed analogs in inducing, entraining, maintaining, modulating and amplifying class MHC-restricted T cell responses, and particularly effector and memory CTL responses to antigen, are described in U.S. Pat. Nos. 6,994,851 (Feb. 7, 2006) and 6,977,074 (Dec. 20, 2005) both entitled "A Method of Inducing a CTL Response"; U.S. Provisional Application No. 60/479,393, filed on Jun. 17, 2003, entitled "METHODS TO CONTROL MHC CLASS I-RESTRICTED IMMUNE RESPONSE"; and U.S. patent application Ser. No. 10/871,707 (Pub. No. 2005 0079152) and Provisional U.S. Patent Application No. 60/640,402 filed on Dec. 29, 2004, both entitled "Methods to elicit, enhance and sustain immune responses against MHC class I-restricted epitopes, for prophylactic or therapeutic purpose". The analogs can also be used in research to obtain further optimized analogs. Numerous housekeeping epitopes are provided in U.S. application Ser. Nos. 10/117,937, filed on Apr. 4, 2002 (Pub. No. 20030220239 A1), and 10/657,022 (20040180354), and in PCT Application No. PCT/US2003/027706 (Pub. No. WO04022709A2), filed on Sep. 5, 2003; and U.S. Provisional Application Nos. 60/282,211, filed on Apr. 6, 2001; 60/337,017, filed on Nov. 7, 2001; 60/363,210 filed on Mar. 7, 2002; and 60/409,123, filed on Sep. 5, 2002; each of which applications is entitled "Epitope Sequences". The analogs can further be used in any of the various modes described in those applications. Epitope clusters, which may comprise or include the instant analogs, are disclosed and more fully defined in U.S. patent application Ser. No. 09/561,571, filed on Apr. 28, 2000, entitled EPITOPE CLUSTERS. Methodology for using and delivering the instant analogs is described in U.S. patent application Ser. No. 09/380,534 and U.S. Pat. No. 6,977,074 (Issued Dec. 20, 2005) and in PCT Application No. PCTUS98/14289 (Pub. No. WO9902183A2), each entitled A "METHOD OF INDUCING A CTL RESPONSE". Beneficial epitope selection principles for such immunotherapeutics are disclosed in U.S. patent application Ser. Nos. 09/560,465, filed on Apr. 28, 2000, 10/026,066 (Pub. No. 20030215425 A1), filed on Dec. 7, 2001, and 10/005,905 filed on Nov. 7, 2001, all entitled "Epitope Synchronization in Antigen Presenting Cells"; 6, 861, 234 (issued 1 Mar. 2005; application Ser. No. 09/561, 074), entitled "Method of Epitope Discovery"; application Ser. No. 09/561,571, filed Apr. 28, 2000, entitled EPITOPE CLUSTERS; application Ser. No. 10/094,699 (Pub. No. 20030046714 A1), filed Mar. 7, 2002, entitled "Anti-Neovasculature Preparations for Cancer"; application Ser. No. 10/117,937 (Pub. No. 20030220239 A1) and PCTUS02/11101 (Pub. No. WO02081646A2), both filed on Apr. 4, 2002, and both entitled "EPITOPE SEQUENCES"; and application Ser. No. 10/657,022 and PCT Application No. PCT/US2003/027706 (Pub. No. WO04022709A2), both filed on Sep. 5, 2003, and both entitled "EPITOPE SEQUENCES". Aspects of the overall design of vaccine plasmids are disclosed in U.S. patent application Ser. No. 09/561,572, filed on Apr. 28, 2000, entitled "Expression Vectors Encoding Epitopes of Target-Associated Antigens" and U.S. patent application Ser. No. 10/292,413 (Pub. No. 20030228634 A1), filed on Nov. 7, 2002, entitled "Expression Vectors Encoding Epitopes of Target-Associated Antigens and Methods for their Design"; U.S. patent application Ser. No. 10/225,568 (Pub No. 2003-0138808), filed on Aug. 20, 2002, PCT Application No. PCT/US2003/026231 (Pub. No. WO 2004/018666), filed on Aug. 19, 2003, both entitled "EXPRESSION VECTORS ENCODING EPITOPES OF TARGET-ASSOCIATED ANTIGENS"; and U.S. Pat. No. 6,709,844, entitled "AVOIDANCE OF UNDESIRABLE REPLICATION INTERMEDIATES IN PLASMID PROPAGATION". Specific antigenic combinations of particular benefit in directing an immune response against particular cancers are disclosed in Provisional U.S. patent Application No. 60/479,554, filed on Jun. 17, 2003 and U.S. patent application Ser. No. 10/871,708, filed on Jun. 17, 2004 and PCT Patent Application No. PCT/US2004/019571 (Pub. No. WO 2004/112825), all entitled "Combinations of tumor-associated antigens in vaccines for various types of cancers". Antigens associated with tumor neovasculature (e.g., PSMA, VEGFR2, Tie-2) are also useful in connection with cancerous diseases, as is disclosed in U.S. patent application Ser. No. 10/094,699 (Pub. No. 20030046714 A1), filed Mar. 7, 2002, entitled "Anti-Neovasculature Preparations for Cancer". Methods to trigger, maintain, and manipulate immune responses by targeted administration of biological response modifiers are disclosed U.S. Provisional Application No. 60/640,727, filed on Dec. 29, 2004. Methods to bypass $CD4^+$ cells in the induction of an immune response are disclosed in U.S. Provisional Application No. 60/640,821, filed on Dec. 29, 2004. Exemplary diseases, organisms and antigens and epitopes associated with target organisms, cells and diseases are described in U.S. Pat. No. 6,977,074 (issued Dec. 20, 2005) filed Feb. 2, 2001 and entitled "METHOD OF INDUCING A CTL RESPONSE". Exemplary methodology is found in U.S. Provisional Application No. 60/580,969, filed on Jun. 17, 2004, and U.S. Patent Application No. 2006-0008468-A1, published on Jan. 12, 2006, both entitled "COMBINATIONS OF TUMOR-ASSOCIATED ANTIGENS IN DIAGNOTISTICS FOR VARIOUS TYPES OF CANCERS". Methodology and compositions are also disclosed in U.S. Provisional Application No. 60/640,598, filed on Dec. 29, 2004, entitled "COMBINATIONS OF TUMOR-ASSOCAITED ANTIGENS IN COMPOSITIONS FOR VARIOUS TYPES OF CANCER". The integration of diagnostic techniques to assess and monitor immune responsiveness with methods of immunization including utilizing the instant analogs is discussed more fully in Provisional U.S. Patent Application No. 60/580,964 filed on Jun. 17, 2004 and U.S. Patent Application No. US-2005-0287068-A1, published on Dec. 29, 2005) both entitled "Improved efficacy of active immunotherapy by integrating diagnostic with therapeutic methods". The immunogenic polypeptide encoding vectors are disclosed in U.S. patent application Ser. No. 10/292,413 (Pub. No. 20030228634 A1), filed on Nov. 7, 2002, entitled Expression Vectors Encoding Epitopes of Target-Associated Antigens and Methods for their Design, and in U.S. Provisional Application No. 60/691,579, filed on Jun. 17, 2005, entitled "Methods and compositions to elicit multivalent immune responses against dominant and subdominant epitopes, expressed on cancer cells and tumor stroma". Additional useful disclosure, including methods and compositions of matter, is found in U.S. Provisional Application No. 60/691,581, filed on Jun. 17, 2005, entitled "Multivalent Entrain-and-Amplify Immunotherapeutics for Carcinoma". Further methodology, compositions, peptides, and peptide analogs are disclosed in U.S. Provisional Application Nos. 60/581,001 and 60/580,962, both filed on Jun. 17, 2004, and respectively entitled "SSX-2 PEPTIDE ANALOGS" and "NY-ESO PEPTIDE ANALOGS." Each of the applications and patents mentioned in the above paragraphs is hereby incorporated by reference in its entirety for all that it teaches. Additional analogs, peptides and methods are disclosed in U.S. Patent Application Publication No. 20060063913, entitled "SSX-2 PEPTIDE ANALOGS"; and U.S. Patent Publication No. 2006-0057673 A1, published on Mar. 16, 2006, entitled "EPITOPE ANALOGS"; and PCT Application Publication No. WO/2006/009920, entitled "EPITOPE ANALOGS"; all filed on Jun. 17, 2005. Further methodology and compositions are disclosed in U.S. Provisional Application No. 60/581,001, filed on Jun. 17, 2004, entitled "SSX-2 PEPTIDE ANALOGS", and to U.S. Provisional Application No. 60/580,962, filed on Jun. 17, 2004, entitled "NY-ESO PEPTIDE ANALOGS"; each of which is incorporated herein by reference in its entirety. As an example, without being limited thereto each reference is incorporated by reference for what it teaches about class I MHC-restricted epitopes, analogs, the design of analogs, uses of epitopes and analogs, methods of using and making epitopes, and the design and use of nucleic acid vectors for their expression. Other applications that are expressly incorporated herein by reference are: U.S. patent application Ser. No. 11/156,253 (Publication No. 20060063913), filed on Jun. 17, 2005, entitled "SSX-2 PEPTIDE ANALOGS"; U.S. patent application Ser. No. 11/155,929, filed on Jun. 17, 2005, entitled "NY-ESO-1 PEPTIDE ANALOGS" (Publication No. 20060094661); U.S. patent application Ser. No. 11/321,967, filed on Dec. 29, 2005, entitled "METHODS TO TRIGGER, MAINTAIN AND MANIPULATE IMMUNE RESPONSES BY TARGETED ADMINISTRATION OF BIOLOGICAL RESPONSE MODIFIERS INTO LYMPHOID ORGANS"; U.S. patent application Ser. No. 11/323,572, filed on Dec. 29, 2005, entitled "METHODS TO ELICIT ENHANCE AND SUSTAIN IMMUNE REPONSES AGAINST MCH CLASS I RESTRICTED EPITOPES, FOR PROPHYLACTIC OR THERAPEUTIC PURPOSES"; U.S. patent application Ser. No. 11/323,520, tiled Dec. 29, 2005, entitled "METHODS TO BYPASS CD4+ CELLS IN THE INDUCTION OF AN IMMUNE RESPONSE"; U.S. patent application Ser. No. 11/323,049, filed Dec. 29, 2005, entitled "COMBINATION OF TUMOR-ASSOCIATED ANTIGENS IN COMPOSITIONS FOR VARIOUS TYPES OF CANCERS"; U.S. patent application Ser. No. 11,323,964, filed Dec. 29, 2005, entitled "COMBINATIONS OF TUMOR-ASSOCIATED ANTIGENS IN DIAGNOSTICS FOR VARIOUS TYPES OF CANCERS"; U.S. Provisional Application Ser. No. 60/691,889, filed on Jun. 17, 2005 entitled "EPITOPE ANALOGS."

VI. Examples

The following examples are included to demonstrate preferred embodiments of the invention in designing plasmids containing immunogenic epitopes of PSMA and PRAME that are capable of eliciting a bivalent immune response. It should be appreciated by those of skill in the art that the methodology disclosed in the examples which follow represent methodologies discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Design of Plasmid Expression Vectors Encoding Immunogens

The plasmids P2 and R2 (also referred to as pCTLR2) contain elements from PSMA (expressed on the neovasculature of a wide range of carcinomas or by prostate carcinoma cells) and PRAME (expressed by cancerous cells), respectively, (FIG. 1). Each insert encompasses a fragment of the antigen's sequence along with multiple copies of an epitope expressed by target cells and addressable via immune mediated attack. Flanking these epitopes are sequences encoding amino acids known to facilitate the processing and generation of epitope peptides in the cellular compartments. In addition, plasmid RP5 encompasses elements from both P2 and R2 with the expressed immunogens adjoined to each other.

The R2 plasmid was constructed following the plasmid construction protocol discussed above and as disclosed in U.S. Provisional Patent Application No. 60/691,889, filed on Jun. 17, 2005 entitled EPITOPE ANALOGS; and U.S. patent application Ser. No. 11/455,278 entitled PRAME EPITOPE ANALOGS, incorporated herein by reference in its entirety. R2, also referred to as pCTLR2, is a recombinant DNA plasmid vaccine which encodes one polypeptide with an HLA A2-specific CTL epitope from PRAME, SLLQHLIGL (SEQ ID NO:5), amino acid residues 425-433, and an epitope cluster region of PRAME, amino acids 422-509 (SEQ ID NO:21). In constructing this plasmid, the DNA sequence encoding the polypeptide in the plasmid is placed under the control of promoter/enhancer sequence from cytomegalovirus (CMVp) which allows efficient transcription of messenger for the polypeptide upon uptake by antigen presenting cells. A bovine growth hormone polyadenylation signal (BGH polyA) at the 3' end of the encoding sequence provides signal for polyadenylation of the messenger to increase its stability as well as translocation out of nucleus into the cytoplasm. To facilitate plasmid transport into the nucleus, a nuclear import sequence (NIS) from Simian virus 40 has been inserted in the plasmid backbone. One copy of CpG immunostimulatory motif is engineered into the plasmid to further boost immune responses. Additionally, two prokaryotic genetic elements in the plasmid are responsible for amplification in *E. coli*, the kanamycin resistance gene (Kan R) and the pMB bacterial origin of replication.

The amino acid sequence (SEQ ID NO:10) of the encoded polypeptide of R2 (pCTLR2) is 150 amino acid residues in length as shown below:

malqsllqhliglsnlthvlypvplesyedihgtlhlerlaylharlrel
lcelgrpsmvwslanpcphcgdrtfydpepilcpcfmpnkrsllqhligl
gdaaysllqhliglis*pekeeqyia*sllqhliglkrpsikrsllqhligl

Amino acid residues 2 to 89 correspond to an epitope cluster region representing PRAME$_{422-509}$ (SEQ ID NO:21). Within this epitope cluster region, a number of potential HLA A2-specific CTL epitopes have been found using a variety of epitope prediction algorithms. Amino acid residues 90-150 are an epitope liberation (synchrotope™) sequence with four embedded copies of the PRAME$_{425-433}$ (SEQ ID NO:5) CTL epitope (boldface). Flanking the defined PRAME CTL epitope are short amino acid sequences that have been shown to play an important role in the processing of the PRAME CTL epitope. In addition, the amino acid sequence ISPEKE-EQYIA (SEQ ID NO:28; corresponding to PRAME amino acid 276-286, in italics) is engineered into this string-of-beads region to facilitate the antibody-based detection of expression of encoded polypeptide.

Example 2

Dominant/Subdominant Hierarchy of Engineered Immunogenic Elements

A study was conducted to assess whether the strategy of engineering elements from different antigens into the same expression vector creates a dominant/subdominant hierarchy amongst those elements.

Four groups of HHD transgenic mice were immunized with plasmids P2, R2, RP5 or a mixture of P2 and R2 plasmids, by direct inoculation into the inguinal lymph nodes of 25 μg/plasmid in 25 μl of PBS to each lymph node at day 1, 4, 15 and 18. Ten days after the boost, splenocytes were stimulated ex vivo with $PRAME_{425\text{-}433}$ (SEQ ID NO:5) or $PSMA_{288\text{-}297}$ (SEQ ID NO:6) peptide and tested against $^{51}$Cr-labeled peptide coated-T2 cells, at various effector to target cell ratios (E:T ratio).

Briefly, target cells expressing antigen on their surface were labeled with a radioactive isotope of chromium ($^{51}$Cr). Splenocytes were then mixed with the target cell and incubated for several hours. After incubation, supernatants were harvested and the cytolytic activity was measured in triplicate samples using a gamma counter. Lysis of antigen-expressing cells releases $^{51}$Cr into the medium. Cell-specific lysis is calculated by comparing lysis (i.e., chromium release) of target cells expressing the antigen(s) of interest or control antigen(s) in the presence or absence of effector cells, and is usually expressed as the % specific lysis.

Figure 2:
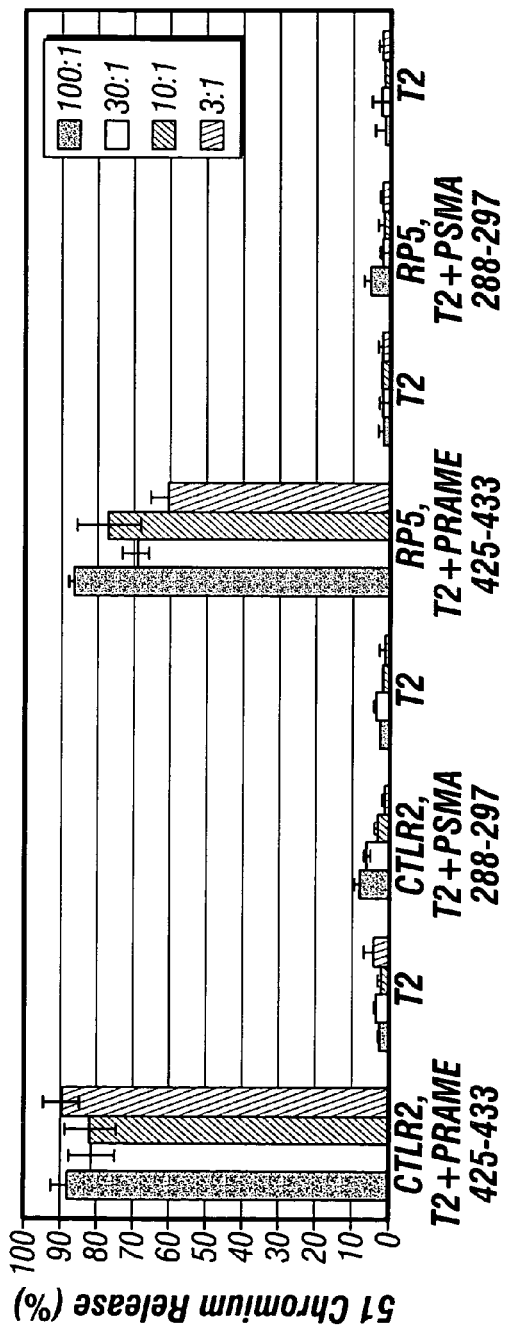
FIG. 2. $^{51}$Cr-release assay depicting the % specific cell lysis in cells expressing the P2, R2, and RP5 plasmids. Data are presented as follows: the x-axis shows target cells used with different effector to target ratio; the y-axis shows the corresponding percentage specific lysis.
Figure 2:
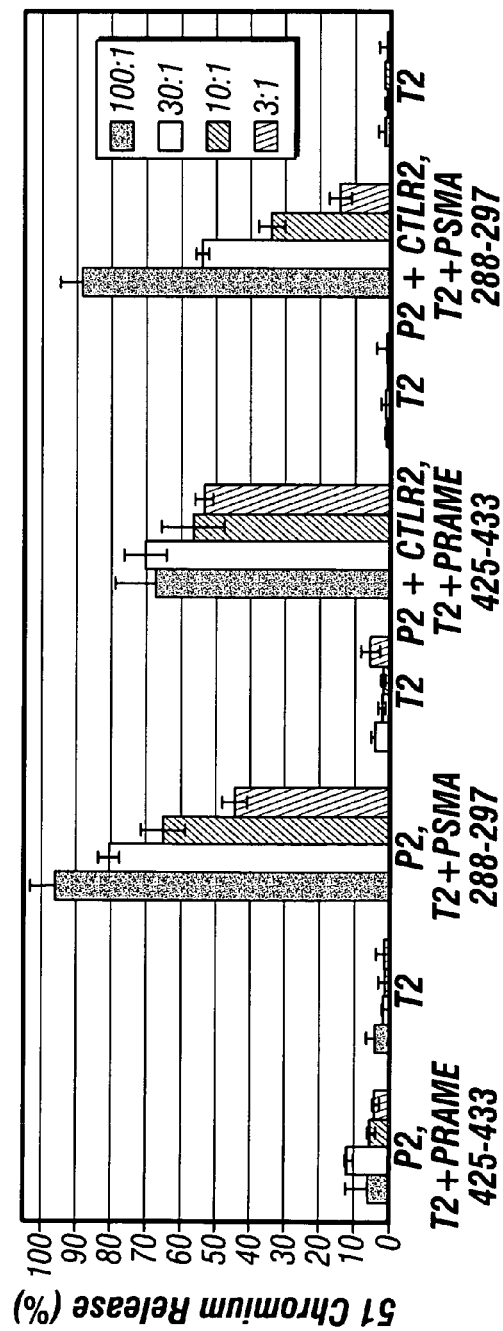

The corrected percent lysis was calculated for each concentration of effector cells, using the mean cpm for each replicate of wells (FIG. 2). Percent specific lysis was calculated using the following formula: Percent release=100×(Experimental release−spontaneous release)/(Maximum release−spontaneous release). Data are presented as follows: the x-axis shows the effector to target ratio; the y-axis shows the corresponding percentage specific lysis. Results are expressed as % specific cytotoxicity (the plasmid R2 is also referred to a CTLR2).

The results show that P2 and R2 separately elicit significant cytotoxic immune responses. However, when the immunogens of P2 and R2 are integrated within the RP5 plasmid, immunity against the PRAME epitope is preserved while response to $PSMA_{288\text{-}297}$ (SEQ ID NO:6) epitope is eclipsed. This indicates that from an immunological standpoint a hierarchy is established between these two epitopes. Admixing P2 and R2 plasmids restores bivalent immunity.

Example 3

Structure of Additional Plasmids

To design expression vectors that result in a more balanced immunity against both PRAME and PSMA epitopes (dominant and subdominant in the context of RP5), a set of immunogens was designed and incorporated within the same plasmid backbone by employing various combinations of the three following methods:
1) The ratio between the copy numbers of the $PRAME_{425\text{-}433}$ (SEQ ID NO:5) (dominant) epitope and that of the $PSMA_{288\text{-}297}$ (subdominant) epitope was adjusted in favor of the latter.
2) The less dominant epitope was placed in the C terminal position so that it would have the proper C-terminus independent of proteasomal processing.
3) The less dominant epitope (PSMA) was mutated (one or multiple copies within the expressed insert) to improve intrinsic immunogenic properties such as binding to, and half-life on, class I MHC.

FIG. 3 shows the design of the various plasmids made. In FIG. 3, "V" corresponds to $PSMA_{266\text{-}297}$ (SEQ ID NO:29) epitopes that carry an I297V mutation.

Example 4

Induction of Bivalent Responses Achieved by Plasmids Encompassing Epitopes from Different Antigens The plasmids designed as described in Example 3 above, were tested to determine their ability to prime a bivalent immune response against the $PRAME_{425\text{-}433}$ (SEQ ID NO:5) and $PSMA_{288\text{-}297}$ (SEQ ID NO:6) tumor associated antigens.

Six groups of HHD transgenic mice (n=8/group) were immunized with plasmids (RP8, RP9, RP10, RP11, RP12, or RP13) carrying inserts depicted in FIG. 3, by direct inoculation into the inguinal lymph nodes of 25 μg in 25 μl of PBS to each lymph node on day 1 and 4. Seven days after the last plasmid injection, on day 11, all of the immunized animals were sacrificed including five naive controls. ELISPOT analysis was conducted by measuring the frequency of IFN-γ producing spot forming colonies (SFC), as described below.

Briefly, spleens were isolated on day 11 from euthanized animals and the mononuclear cells, after density centrifugation (Lympholyte Mammal, Cedarlane Labs, Burlington, N.C.), were resuspended in HL-1 medium. Splenocytes ($5\times10^5$ or $2.5\times10^5$ cells per well) were incubated with 10 μg of $PSMA_{288\text{-}297}$ (SEQ ID NO:6) or $PRAME_{425\text{-}433}$ (SEQ ID NO:5), natural peptide in triplicate wells of a 96 well filter membrane plates (Multi-screen IP membrane 96-well plate, Millipore, Mass.). Samples were incubated for 42 hours at 37° C. with 5% $CO_2$ and 100% humidity prior to development. Mouse IFN-γ coating antibody (IFN-γ antibody pair, U-CyTech Biosciences, The Netherlands) was used as a coating reagent prior to incubation with splenocytes, followed by the accompanied biotinylated detection antibody. GABA conjugate and proprietary substrates from U-CyTech Biosciences were used for IFN-γ spot development. The CTL response in immunized animals was measured 24 hours after development on the AID International plate reader using ELISpot Reader software version 3.2.3 calibrated for IFN-γ spot analysis.

Figure 4:
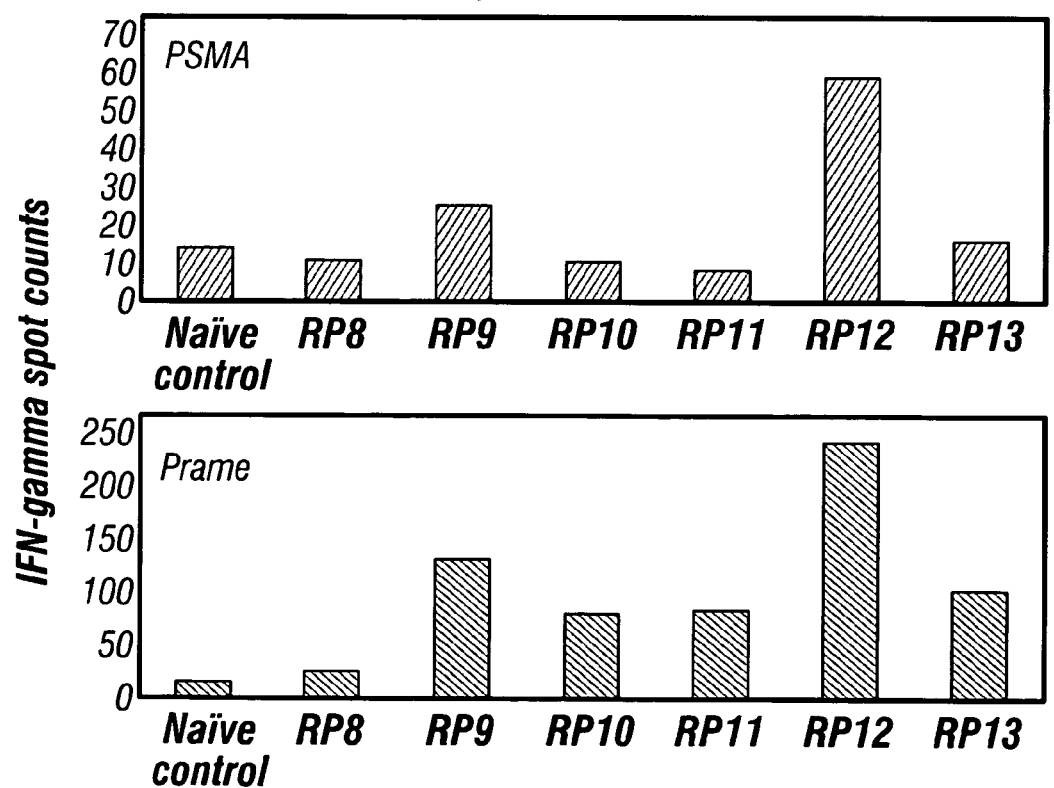
FIG. 4. ELISpot analysis of PRAME and PSMA depicting induction of bivalent responses achieved by plasmids encompassing epitopes from the different antigens depicted in FIG. 3. Animals were immunized with 2 injections of PRAME/PSMA bivalent plasmid (1 mg/ml) in bilateral lymph nodes. $5\times10^5$ isolated splenocytes were incubated with 10 μg $PSMA_{288-297}$ (SEQ ID NO:6):natural peptide or 10 μg $PRAME_{425-433}$ (SEQ ID NO:5) natural peptide for 42 hours prior to development. Graphs represent average +/− SEM.

The results depicted in FIG. 4 show the average IFN-γ spot count for each experimental group. The data are presented as the frequency of IFN-γ spots (representing a colony of IFN-γ secreting cells) per treatment, as the average of individual animal responses +/− the standard deviation (Std). Data generated from splenocytes isolated from immunized or naive mice and stimulated with the $PSMA^{288\text{-}297}$ native peptide indicated that RP12 induced the strongest immunity to the $PSMA_{288\text{-}297}$ antigen (55.8+/−1.6 INF-γ spots) as compared to the naive control (12.8+2.4 IFN-γ spots) or the other treatment groups. This represented a 5-fold enhanced PSMA immune response with the RP12 plasmid.

In addition, data generated from splenocytes isolated from immunized or naive mice and stimulated with the $PRAME_{425\text{-}433}$ native peptide also demonstrated that animals immunized with RP12 showed the strongest immune response to the PRAME$_{425-433}$ antigen (234.5+3.7 IFN-γ spots) as compared to the naive controls (8.5+2.8 IFN-γ spots) or the other treatment groups. This represented a greater than 20-fold increased PRAME response with the RP12 plasmid.

Overall, the results depicted in FIG. 4 show induction of a strong bivalent immunity against both PRAME and PSMA epitopes by the plasmid RP12. Some bivalent immunity against both PRAME and PSMA epitopes was observed with RP9 and to a lesser extent RP13, RP10, RP11 and RP8—all having a more potent representation of the PSMA epitope relative to PRAME epitope as compared to the plasmid RP5 (FIG. 2). This observation is apparently due in part to use of the I297V analogue of PSMA.

Example 5

Induction of a Bivalent Response by the RP12 Plasmid

Based on the comparison in Example of 4 of the six plasmids (RP8, RP9, RP10, RP11, RP12, and RP13), RP12 was selected for further analysis, as it was the only plasmid that primed a robust, bivalent immune response against both PRAME$_{425-433}$ (SEQ ID NO:5) and PSMA$_{288-297}$ (SEQ ID NO:6).

Two representative HHD transgenic mice were immunized with RP12 plasmid carrying an insert (depicted in FIG. 3) by direct inoculation into the inguinal lymph nodes of 25 μg in 25 μl of PBS to each lymph node at day 1, 4, 15 and 18. Ten days after the last plasmid injection, the frequency of PRAME and PSMA epitope-specific CD8$^+$ T cells was measured by tetramer staining of peripheral blood mononuclear cells and co-staining for CD8 expression.

Briefly, mononuclear cells were isolated from peripheral blood after density centrifugation (Lympholyte Mammal, Cedarlane Labs) and stained with HLA-A*0201 PRAME MHC tetramer (Beckman Coulter, T02001), and HLA-A*0201 PSMA MHC tetramer (Beckman Coulter, T02001). These cells were then co-stained using FITC conjugated rat anti-mouse CD8a (Ly-2) monoclonal antibody (BD Biosciences, 553031). Data were collected using a BD FACS Calibur flow cytometer and analyzed using Cellquest software by gating on the lymphocyte population and calculating the percent of tetramer positive cells within the CD8$^+$ population.

Figure 5:
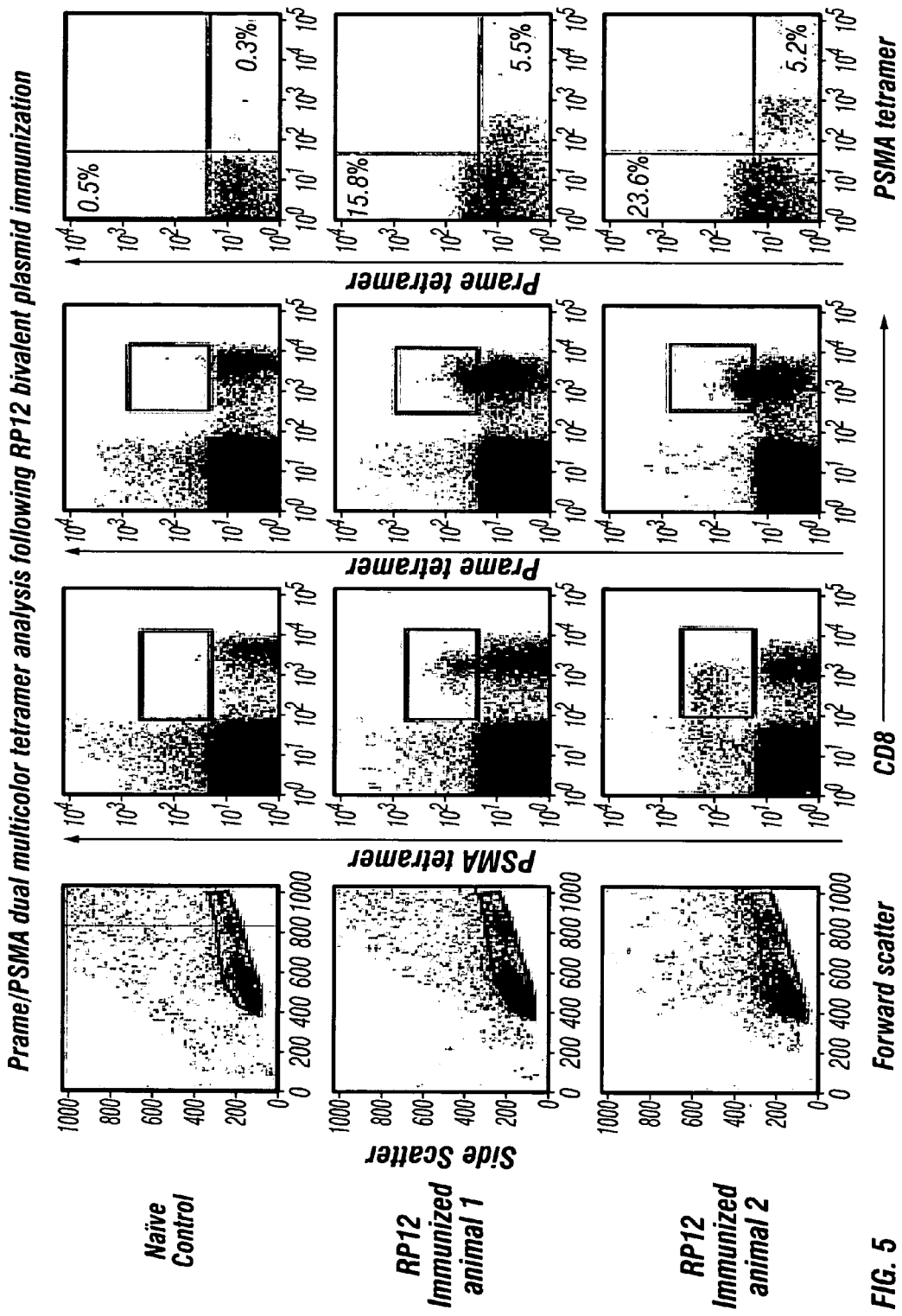
FIG. 5. Tetramer analysis of PRAME and PSMA following RP12 bivalent plasmid immunization. The data shows a bivalent immune response to PRAME and PSMA with relative dominance of the response against the PRAME epitope in plasmid-only primed mice.

The results depicted in FIG. 5, show that following intranodal plasmid immunization, the RP12 plasmid elicited dual immunity and the frequency of PRAME$_{425-433}$ specific T cells was several fold higher than that of T cells specific for the PSMA subdominant epitope Example 6

Bivalent Immune Response in Mice Primed with PRAME and PSMA Plasmid and Boosted with Peptide To determine whether immunization with the plasmids RP12 and RP8 could induce a bivalent response against the tumor associated antigens Prame$_{425-433}$ and PSMA$_{288-297}$, following peptide boost with the PSMA$_{288-297}$ I297V (SEQ ID NO:7) analogue, a tetramer analysis of immunized animals was conducted.

HHD transgenic mice were immunized with RP8 or RP12 plasmids carrying inserts depicted in FIG. 3, by direct inoculation into the inguinal lymph nodes of 100 μg in 25 μl of PBS to each lymph node at day 1, 4, 15 and 18. On days 29 and 32, the mice were boosted with 25 μg of PSMA$_{288-297}$ peptide analogue (I297V). One day before initiation of peptide boost and ten days after the completion of plasmid boost, the frequency of PRAME and PSMA epitope-specific T cells was measured by tetramer staining (as described above) and compared to tetramer results seven days following the last peptide boost.

Figure 6:
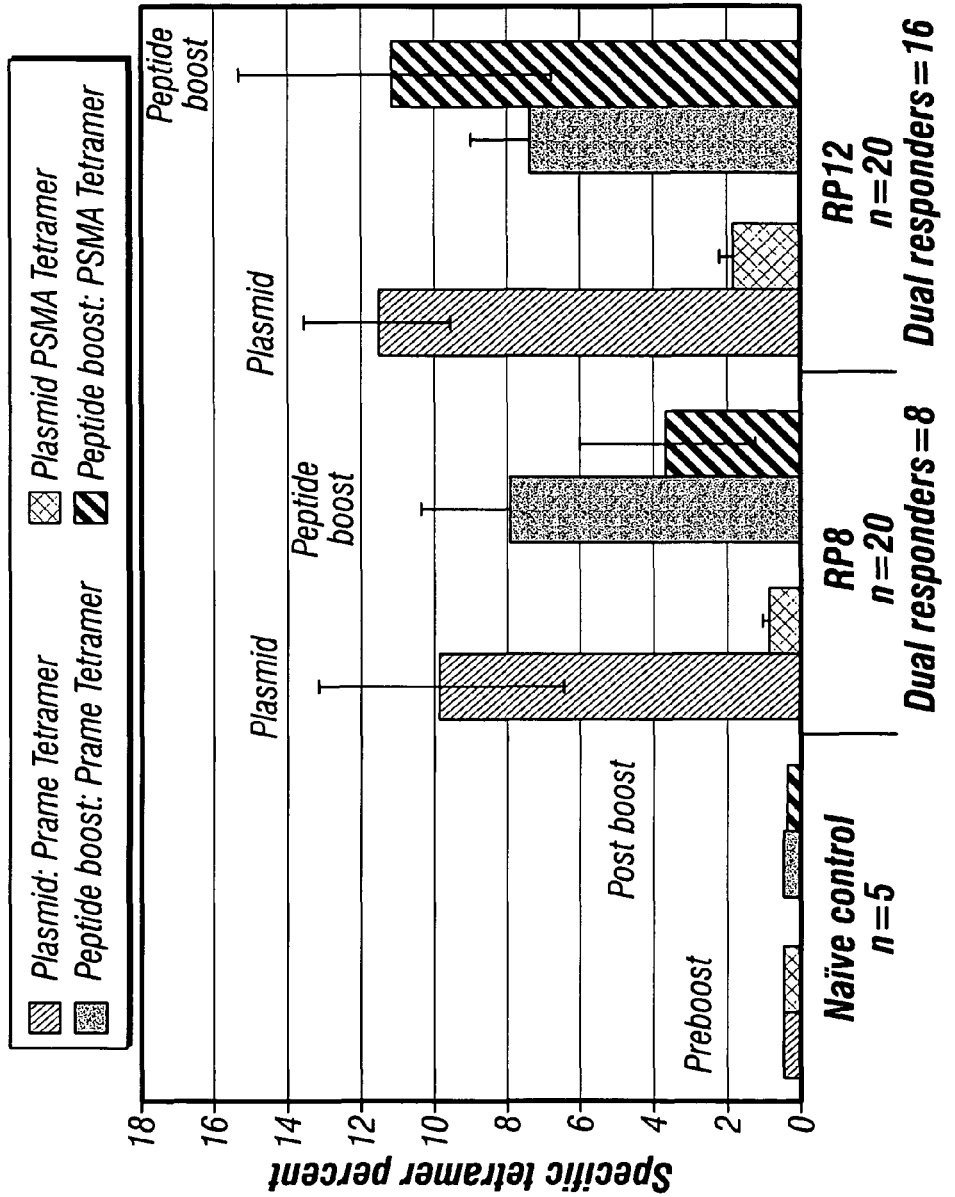
FIGS. 6-6B. Tetramer analysis of PRAME and PSMA in mice receiving RP12 or RP8 bivalent plasmid immunization followed by a PSMA$_{288-297}$ (I297V) (SEQ ID NO:7) peptide analogue boost (FIG. 6). Tetramer analysis of PRAME and PSMA in individual animals following RP12 or RP8 bivalent plasmid immunization and PSMA$_{288-297}$ (I297V) (SEQ ID NO:7) peptide analogue boost (FIG. 6B).

The results shown in FIG. 6, as mean ±SEM of specific CD8$^+$T cell frequency showed that RP12 plasmid elicits a slightly higher PSMA-specific immunity than RP8 prior to peptide boost. In addition, in both the case of RP12 and RP8, the immunity against PRAME was found to be dominant prior to peptide boost. However, after boost with the PSMA subdominant epitope, the immune response against PRAME and PSMA displayed a more balanced profile, particularly in the case of RP12, indicating the benefit of strategies to elicit equilibrated immune responses against epitopes of different immune hierarchy.

Figure 6B:
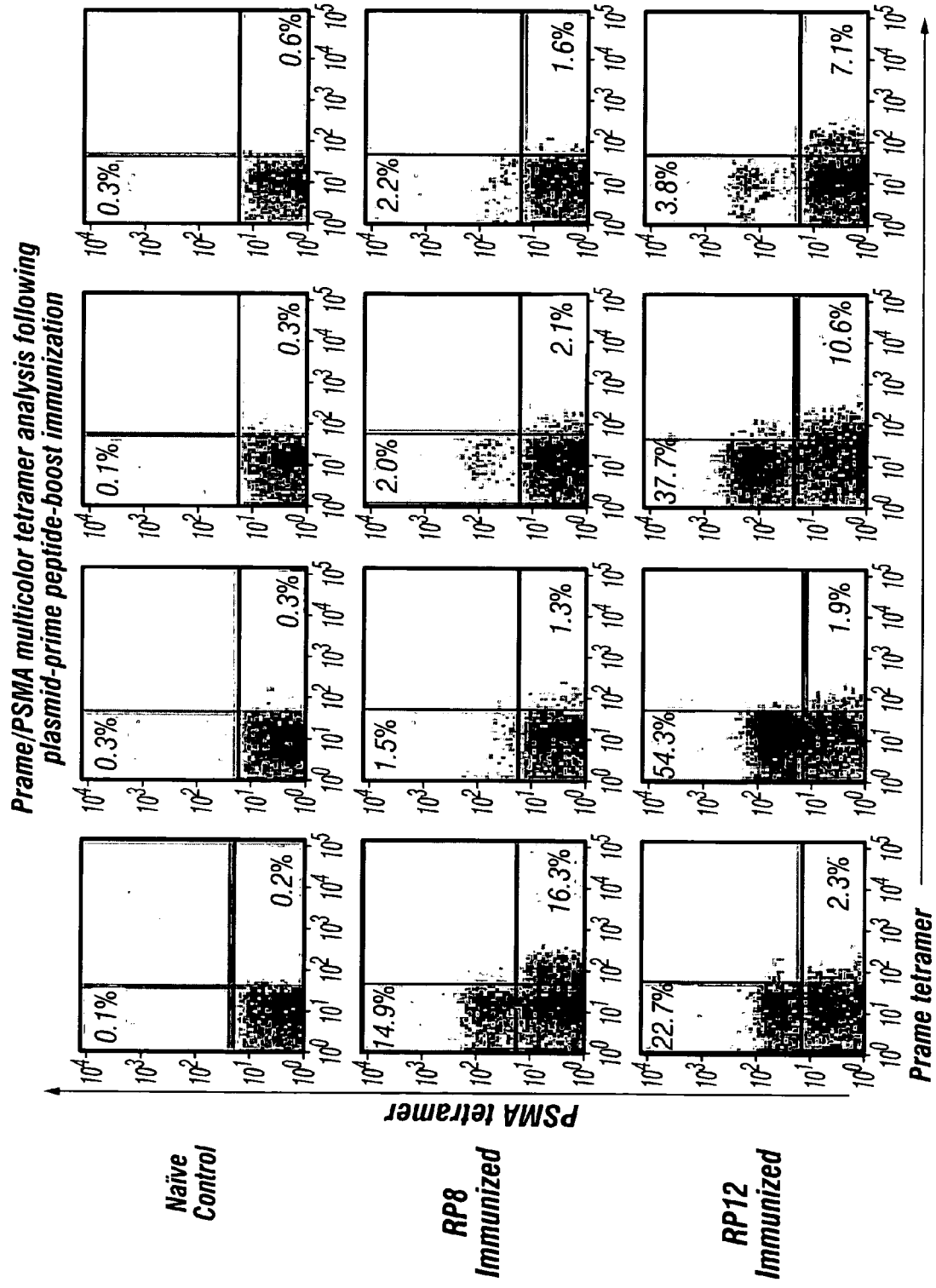

FIG. 6B shows immune responses to PRAME and PSMA in three representative mice from each group and further illustrate the enhanced bivalent response elicited by the RP12 plasmid and the PSMA (I297V) peptide boost.

Example 7

Bivalent Immune Response After PSMA Peptide Boost and Subsequent PRAME Peptide Boost It was examined whether immunization with the plasmids RP12 and RP8 could induce a bivalent response against the PRAME$_{425-433}$ (SEQ ID NO:5) and PSMA$_{288-297}$ (SEQ ID NO:6) epitopes those tumor associated antigens, following a first peptide boost with the PSMA$_{288-297}$ I297V (SEQ ID NO:7) analogue and a second boosting with PRAME$_{425-433}$ L426Nva, L433Nle (SEQ ID NO:30) peptide analogue.

Figure 7:
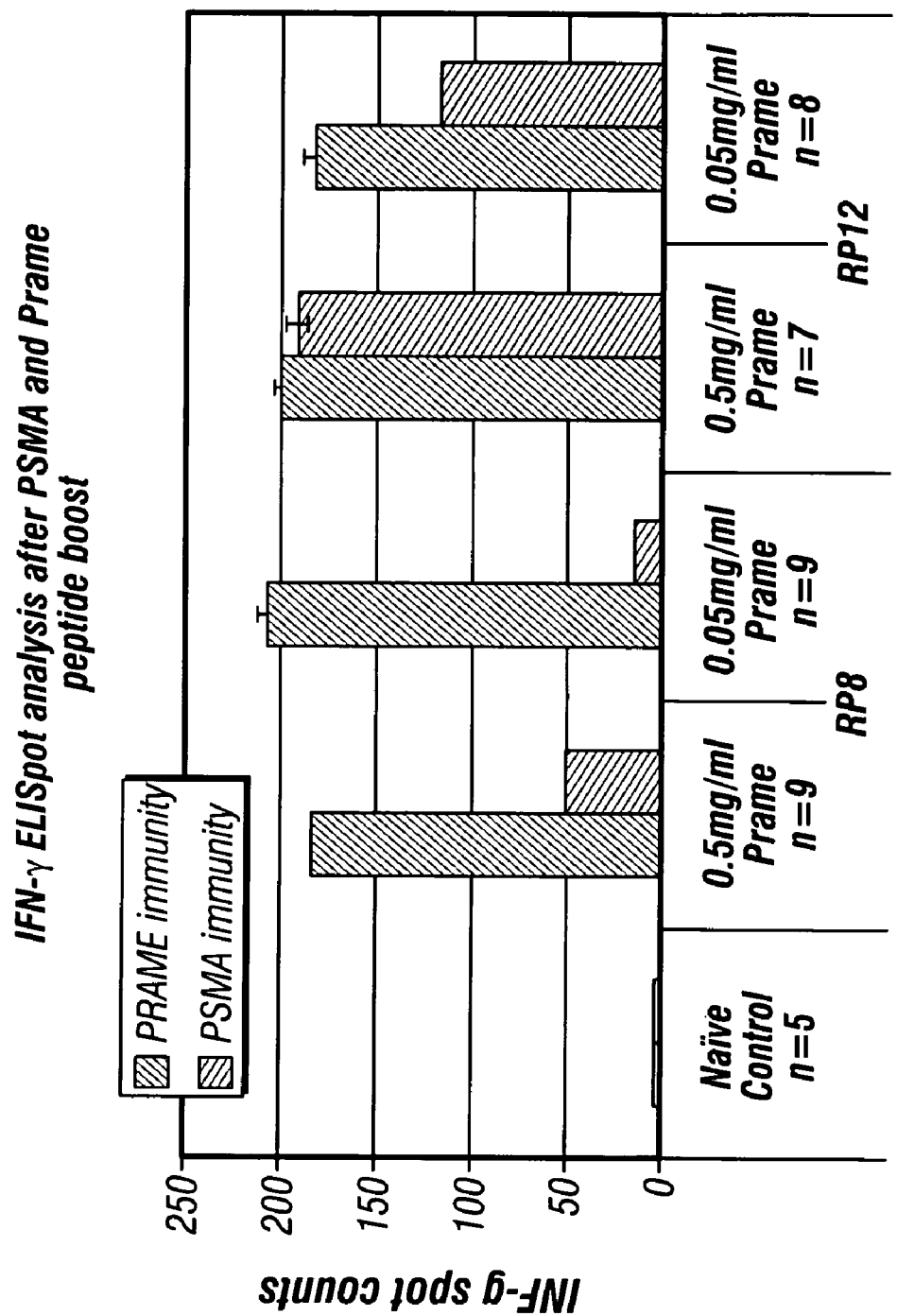
FIG. 7. ELISpot analysis in animals primed with RP12 or RP8 and boosted with PSMA$_{288-297}$ (I297V) (SEQ ID NO:7) and PRAME$_{425-433}$ (L426Nva, L433Nle) (SEQ ID NO:30) peptide analogues.

Mice were immunized with 4 injections of the RP8 or RP12 plasmid (4 mg/ml) by direct inoculation into the inguinal lymph nodes at day 1, 4, 15 and 18. On days 29 and 32, the mice were boosted with PSMA$_{288-297}$ I297V peptide analogue (0.5 mg/ml), followed by a second boost on day 42 and 59 with Prame$_{425-433}$ L426Nva, L433Nle peptide analogue at 0.5 mg/ml and 0.05 mg/ml respectively. Mice were sacrificed and an ELISPOT analysis (FIG. 7) was conducted as follows.

Briefly, spleens were isolated ten days following the last Prame$_{425-433}$ L426Nva, L433Nle peptide injection from euthanized animals and the mononuclear cells, after density centrifugation (Lympholyte Mammal, Cedarlane Labs, Burlington, N.C.), were resuspended in HL-1 medium. Splenocytes (2×10$^5$ cells per well) were incubated with 10 μg of PSMA$_{288-297}$ or PRAME$_{425-433}$, natural peptide in triplicate wells of a 96 well filter membrane plates (Multi-screen IP membrane 96-well plate, Millipore, Mass.). Samples were incubated for 72 hours at 37° C. with 5% CO$_2$ and 100% humidity prior to development. Mouse IFN-γ coating antibody (IFN-γ antibody pair, U-CyTech Biosciences, The Netherlands) was used as a coating reagent prior to incubation with splenocytes, followed by the accompanied biotinylated detection antibody. GABA conjugate and various substrates from U-CyTech Biosciences were used for IFN-γ spot development. The CTL response in immunized animals was measured 24 hours after development on the AID International plate reader using ELISpot Reader software version 3.2.3 calibrated for IFN-γ spot analysis.

The results show that RP12 plasmid elicits a higher PSMA-specific immunity than RP8 at all doses tested. For both the RP12 and RP8 plasmids, the immunity against PRAME was found to be dominant at all doses tested. Also, the RP12 plasmid showed a strong balanced immune response against PRAME and PSMA following boost with the PSMA and PRAME epitopes.

The invention claimed is:

1. An engineered nucleic acid construct encoding a polypeptide comprising: a cross-reactive analogue differing from CTL epitope $PSMA_{288-297}$ (SEQ ID NO:6) by only 1-3 substitutions, wherein the cross-reactive analogue of CTL epitope $PSMA_{288-297}$ (SEQ ID NO:6) comprises an I297V substitution; and
one or more copies of CTL epitope $PRAME_{425-433}$ (SEQ ID NO:5), or a cross-reactive analogue differing from SEQ ID NO:5 by only 1-3 substitutions.

2. The nucleic acid construct of claim 1 wherein one or both epitopes are encoded within a liberation sequence.

3. The nucleic acid construct of claim 1 wherein said polypeptide further comprises a sequence encoding one or more epitope clusters.

4. The nucleic acid construct of claim 3 comprising a PRAME epitope cluster.

5. The nucleic acid construct of claim 4 wherein said epitope cluster consist essentially of amino acids 422-509 of PRAME (SEQ ID NO:21).

6. The nucleic acid construct of claim 3 comprising a PSMA epitope cluster.

7. The nucleic acid construct of claim 6 wherein said epitope cluster is chosen from the group consisting of amino acids 3-45 of PSMA (SEQ ID NO:22) and 217-297 of PSMA (SEQ ID NO:23).

8. The nucleic acid construct of claim 1 further comprising a nuclear import sequence.

9. The nucleic acid construct of claim 1 further comprising a promoter.

10. The nucleic acid construct of claim 9 wherein the promoter is a cytomegalovirus (CMV) promoter.

11. The nucleic acid construct of claim 1 further comprising a poly-A sequence.

12. The nucleic acid construct of claim 1 further comprising one or more of a CpG immunostimulatory motif.

13. The nucleic acid construct of claim 2, wherein both epitopes are encoded within a liberation sequence.

14. The nucleic acid construct of claim 1 wherein the encoded polypeptide is SEQ ID NO:2.

15. The nucleic acid construct of claim 13 wherein the liberation sequence of the PRAME and PSMA epitopes is located in the C-terminal portion of the encoded polypeptide.

16. The nucleic acid construct of claim 15 wherein the encoded polypeptide is SEQ ID NO:4.

17. An immunogenic composition comprising the nucleic acid construct of claim 1.

18. A method of obtaining an immune response in an individual having cancer comprising the step of administering an effective amount of the composition of claim 17.

19. The method of claim 18 wherein the composition is administered intranodally.

20. The method of claim 18 wherein the individual has a cancer that expresses PRAME, PSMA, or both in neoplastic cells or tumor-associated neovasculature cells.

21. A method of obtaining an immune response in an individual having cancer comprising the steps of:
administering an effective amount of the composition of claim 17 to induce an immune response; and amplifying the immune response by boosting with at least one peptide analogue corresponding to an epitope encoded by the nucleic acid construct of said composition.

22. The method of claim 21 wherein the individual has a cancer that expresses PRAME on cancer cells and PSMA on tumor-associated vasculature cells.

23. The method of claim 21 wherein the individual has a cancer that expresses PRAME, PSMA, or both in neoplastic cells or tumor-associated neovasculature cells.

24. The nucleic acid construct of claim 13 wherein the liberation sequence of the PRAME and PSMA epitope is located in the N-terminal portion of the encoded polypeptide.

25. An engineered nucleic acid construct encoding a polypeptide comprising one or more copies of CTL epitope $PSMA_{288-297}$ (SEQ ID NO:6), or a cross-reactive analogue differing from SEQ ID NO:6 by only 1-3 substitutions, and one or more copies of CTL epitope $PRAME_{425-433}$ (SEQ ID NO:5), or a cross-reactive analogue differing from SEQ ID NO:5 by only 1-3 substitutions, the construct further comprising a nuclear import sequence.

26. The nucleic acid construct of claim 25, wherein the polypeptide does not comprise a whole PSMA antigen (SEQ ID NO:19) or a whole PRAME antigen (SEQ ID NO:20).

27. The nucleic acid construct of claim 25 wherein one or both epitopes are encoded within a liberation sequence.

28. The nucleic acid construct of claim 27, wherein both epitopes are encoded within a liberation sequence.

29. The nucleic acid construct of claim 25, wherein said polypeptide further comprises a sequence encoding one or more epitope clusters.

30. The nucleic acid construct of claim 29 comprising a PRAME epitope cluster.

31. The nucleic acid construct of claim 30, wherein said epitope cluster consist essentially of amino acids 422-509 of PRAME (SEQ ID NO:21).

32. The nucleic acid construct of claim 29 comprising a PSMA epitope cluster.

33. The nucleic acid construct of claim 32, wherein said epitope cluster is chosen from the group consisting of amino acids 3-45 of PSMA (SEQ ID NO:22) and 217-297 of PSMA (SEQ ID NO:23).

34. The nucleic acid construct of claim 25 further comprising a promoter.

35. The nucleic acid construct of claim 34, wherein the promoter is a cytomegalovirus (CMV) promoter.

36. The nucleic acid construct of claim 25 further comprising a poly-A sequence.

37. The nucleic acid construct of claim 25 further comprising one or more of a CpG immunostimulatory motif.

38. The nucleic acid construct of claim 28, wherein the liberation sequence of the PRAME and PSMA epitope is located in the N-terminal portion of the encoded polypeptide.

39. The nucleic acid construct of claim 28 wherein the liberation sequence of the PRAME and PSMA epitopes is located in the C-terminal portion of the encoded polypeptide.

40. An immunogenic composition comprising the nucleic acid construct of claim 25.

41. A method of obtaining an immune response in an individual having cancer comprising the step of administering an effective amount of the composition of claim 40.

42. The method of claim 41 wherein the composition is administered intranodally.

43. The method of claim 41 wherein the individual has a cancer that expresses PRAME, PSMA, or both in neoplastic cells or tumor-associated neovasculature cells.

44. A method of obtaining an immune response in an individual having cancer comprising the steps of:
    administering an effective amount of the composition of claim 40 to induce an immune response; and amplifying the immune response by boosting with at least one peptide analogue corresponding to an epitope encoded by the nucleic acid construct of said composition.

45. The method of claim 44 wherein the individual has a cancer that expresses PRAME on cancer cells and PSMA on tumor-associated vasculature cells.

46. The method of claim 44 wherein the individual has a cancer that expresses PRAME, PSMA, or both in neoplastic cells or tumor-associated neovasculature cells.

47. An engineered nucleic acid construct encoding a polypeptide comprising the sequence of SEQ ID NO:2.

48. The nucleic acid construct of claim 47 further comprising a nuclear import sequence.

49. The nucleic acid construct of claim 47 further comprising a promoter.

50. The nucleic acid construct of claim 49 wherein the promoter is a cytomegalovirus (CMV) promoter.

51. The nucleic acid construct of claim 47 further comprising a poly-A sequence.

52. The nucleic acid construct of claim 47 further comprising one or more of a CpG immunostimulatory motif.

53. An immunogenic composition comprising the nucleic acid construct of claim 47.

54. A method of obtaining an immune response in an individual having cancer comprising the step of administering an effective amount of the composition of claim 53.

55. The method of claim 54 wherein the composition is administered intranodally.

56. The method of claim 54 wherein the individual has a cancer that expresses PRAME, PSMA, or both in neoplastic cells or tumor-associated neovasculature cells.

57. A method of obtaining an immune response in an individual having cancer comprising the steps of:
    administering an effective amount of the composition of claim 53 to induce an immune response; and amplifying the immune response by boosting with at least one peptide analogue corresponding to an epitope encoded by the nucleic acid construct of said composition.

58. The method of claim 57 wherein the individual has a cancer that expresses PRAME on cancer cells and PSMA on tumor-associated vasculature cells.

59. The method of claim 57 wherein the individual has a cancer that expresses PRAME, PSMA, or both in neoplastic cells or tumor-associated neovasculature cells.

60. An engineered nucleic acid construct encoding a polypeptide comprising the sequence of SEQ ID NO:4.

61. The nucleic acid construct of claim 60 further comprising a nuclear import sequence.

62. The nucleic acid construct of claim 60 further comprising a promoter.

63. The nucleic acid construct of claim 62 wherein the promoter is a cytomegalovirus (CMV) promoter.

64. The nucleic acid construct of claim 60 further comprising a poly-A sequence.

65. The nucleic acid construct of claim 60 further comprising one or more of a CpG immunostimulatory motif.

66. An immunogenic composition comprising the nucleic acid construct of claim 60.

67. A method of obtaining an immune response in an individual having cancer comprising the step of administering an effective amount of the composition of claim 66.

68. The method of claim 67 wherein the composition is administered intranodally.

69. The method of claim 67 wherein the individual has a cancer that expresses PRAME, PSMA, or both in neoplastic cells or tumor-associated neovasculature cells.

70. A method of obtaining an immune response in an individual having cancer comprising the steps of:
    administering an effective amount of the composition of claim 66 to induce an immune response; and amplifying the immune response by boosting with at least one peptide analogue corresponding to an epitope encoded by the nucleic acid construct of said composition.

71. The method of claim 70 wherein the individual has a cancer that expresses PRAME on cancer cells and PSMA on tumor-associated vasculature cells.

72. The method of claim 70 wherein the individual has a cancer that expresses PRAME, PSMA, or both in neoplastic cells or tumor-associated neovasculature cells.

* * * * *

SEQUENCE LISTING

<160> NUMBER OF SEQ ID NOS: 30

<210> SEQ ID NO 1
<211> LENGTH: 3950
<212> TYPE: DNA
<213> ORGANISM: Homo sapiens

<400> SEQUENCE: 1

| | | | | | |
|---|---|---|---|---|---|
| cgttgacatt | gattattgac | tagttattaa | tagtaatcaa | ttacggggtc | attagttcat | 60 |
| agcccatata | tggagttccg | cgttacataa | cttacggtaa | atgcccgcc | tggctgaccg | 120 |
| cccaacgacc | cccgcccatt | gacgtcaata | atgacgtatg | ttcccatagt | aacgccaata | 180 |
| gggactttcc | attgacgtca | atgggtggag | tatttacggt | aaactgccca | cttggcagta | 240 |
| catcaagtgt | atcatatgcc | aagtacgccc | cctattgacg | tcaatgacgg | taaatggccc | 300 |
| gcctggcatt | atgcccagta | catgacctta | tgggactttc | ctacttggca | gtacatctac | 360 |
| gtattagtca | tcgctattac | catggtgatg | cggttttggc | agtacatcaa | tgggcgtgga | 420 |
| tagcggtttg | actcacgggg | atttccaagt | ctccacccca | ttgacgtcaa | tgggagtttg | 480 |
| ttttggcacc | aaaatcaacg | ggactttcca | aaatgtcgta | acaactccgc | cccattgacg | 540 |
| caaatgggcg | gtaggcgtgt | acggtgggag | gtctatataa | gcagagctct | ctggctaact | 600 |
| agagaaccca | ctgcttactg | gcttatcgaa | attaatacga | ctcactatag | ggagacccaa | 660 |
| gctggctagc | gtttaaactt | aagccaccat | gaagaggcca | agtattaaga | ggagtctcct | 720 |
| gcaacacctc | atcgggcttg | ccctgcagag | tctcttgcag | cacctcatcg | ggctgagcaa | 780 |
| tctgacccac | gtgctgtatc | ctgtccccct | ggagagttat | gaggacatcc | atggtaccct | 840 |
| ccacctggag | aggcttgcct | atctgcatgc | caggctcagg | gagttgctgt | gtgagttggg | 900 |
| gcggcccagc | atggtctggc | ttagtgccaa | cccctgtcct | cactgtgggg | acagaacctt | 960 |
| ctatgacccg | gagcccatcc | tgtgccctg | tttcatgcct | aacaagctta | atctccttca | 1020 |
| cgaaaccgac | tcggctgtgg | ccaccgcgcg | ccgcccgcgc | tggctgtgcg | ctggggcgct | 1080 |
| ggtgctggcg | ggtggcttct | ttctcctcgg | cttcctcttc | gggtggttta | taaaaagcgc | 1140 |
| tcagctggca | ggggccaaag | gagtcattct | ctactccgac | cctgctgact | actttgctcc | 1200 |
| tggggtgaag | tcctatccag | atggttggaa | tcttcctgga | ggtggtgtcc | agcgtggaaa | 1260 |
| tatcctaaat | ctgaatggtg | caggagaccc | tctcacacca | ggttacccag | caaatgaata | 1320 |
| tgcttatagg | cgtggaattg | cagaggctgt | tggtcttcca | agtattcctg | ttcatcctat | 1380 |
| tcgaaagggc | cttccaagta | ttcctgttca | tccaattctc | gtcggtcttc | caagtattcc | 1440 |
| tgttcatcca | attaagcgca | tttccccgga | gaaggaagag | cagtatatcg | ccaagcgcgg | 1500 |
| tcttccaagt | attcctgttc | atccaattaa | gaggccaagt | attaagaggg | gtcttccaag | 1560 |
| tattcctgtt | catccagttt | agtgagaatt | ctgcagatat | ccatcacact | ggcggccgct | 1620 |
| cgagtctaga | gggcccgttt | aaacccgctg | atcagcctcg | actgtgcctt | ctagttgcca | 1680 |
| gccatctgtt | gtttgcccct | ccccgtgcc | ttccttgacc | ctggaaggtg | ccactcccac | 1740 |
| tgtcctttcc | taataaaatg | aggaaattgc | atcgcattgt | ctgagtaggt | gtcattctat | 1800 |
| tctggggggt | ggggtggggc | aggacagcaa | gggggaggat | tgggaagaca | atagcaggca | 1860 |
| tgctggggat | gcggtgggct | ctatggcttc | tactgggcgg | ttttatggac | agcaagcgaa | 1920 |
| ccggaattgc | cagctggggc | gccctctggt | aaggttggga | agccctgcaa | agtaaactgg | 1980 |

```
atggctttct tgccgccaag gatctgatgg cgcagggat caagtctga tcaagagaca    2040
ggatgaggat cgtttcgcat gattgaacaa gatggattgc acgcaggttc tccggccgct    2100
tgggtggaga ggctattcgg ctatgactgg gcacaacaga caatcggctg ctctgatgcc    2160
gccgtgttcc ggctgtcagc gcagggggcgc ccggttcttt ttgtcaagac cgacctgtcc    2220
ggtgccctga tgaactgca agacgaggca gcgcggctat cgtggctggc acgacgggc    2280
gttccttgcg cagctgtgct cgacgttgtc actgaagcgg gaagggactg gctgctattg    2340
ggcgaagtgc cggggcagga tctcctgtca tctcaccttg ctcctgccga gaaagtatcc    2400
atcatggctg atgcaatgcg gcggctgcat acgcttgatc cggctacctg cccattcgac    2460
caccaagcga acatcgcat cgagcgagca cgtactcgga tggaagccgg tcttgtcgat    2520
caggatgatc tggacgaaga gcatcagggg ctcgcgccag ccgaactgtt cgccaggctc    2580
aaggcgagca tgcccgacgg cgaggatctc gtcgtgaccc atggcgatgc ctgcttgccg    2640
aatatcatgg tggaaaatgg ccgcttttct ggattcatcg actgtggccg gctgggtgtg    2700
gcggaccgct atcaggacat agcgttggct acccgtgata ttgctgaaga gcttggcggc    2760
gaatgggctg accgcttcct cgtgctttac ggtatcgccg ctcccgattc gcagcgcatc    2820
gccttctatc gccttcttga cgagttcttc tgaattatta cgcttacaa tttcctgatg    2880
cggtattttc tccttacgca tctgtgcggt atttcacacc gcatcaggtg cacttttcg    2940
gggaaatgtg cgcggaaccc ctatttgttt attttctaa atacattcaa atatgtatcc    3000
gctcatgaga caataaccct gataaatgct tcaataatag cacgtgctaa aacttcattt    3060
ttaatttaaa aggatctagg tgaagatcct ttttgataat ctccggaaga gtcaagaaca    3120
tgtgagcaaa aggccagcaa aaggccagga accgtaaaaa ggccgcgttg ctggcgtttt    3180
tccataggct ccgcccccct gacgagcatc acaaaaatcg acgctcaagt cagaggtggc    3240
gaaacccgac aggactataa agataccagg cgtttccccc tggaagctcc ctcgtgcgct    3300
ctcctgttcc gaccctgccg cttaccggat acctgtccgc ctttctccct cgggaagcg    3360
tggcgctttc tcatagctca cgctgtaggt atctcagttc ggtgtaggtc gttcgctcca    3420
agctgggctg tgtgcacgaa ccccccgttc agcccgaccg ctgcgcctta tccggtaact    3480
atcgtcttga gtccaacccg gtaagacacg acttatcgcc actggcagca gccactggta    3540
acaggattag cagagcgagg tatgtaggcg gtgctacaga gttcttgaag tggtggccta    3600
actacggcta cactagaaga acagtatttg gtatctgcgc tctgctgaag ccagttacct    3660
tcggaaaaag agttggtagc tcttgatccg gcaaacaaac caccgctggt agcggtggtt    3720
tttttgtttg caagcagcag attacgcgca gaaaaaaagg atctcaagaa gatcctttga    3780
tcttttctac ggggtctgac gctcagtgga acgaaaactc acgttaaggg attttggtcc    3840
ggccggaaac gtttggttgc tgactaattg agatgcatgc tttgcatact tctgcctgct    3900
ggggagcctg gggactttcc acacctcgcg atgtacgggc cagatatacg                3950
```

<210> SEQ ID NO 2  
<211> LENGTH: 297  
<212> TYPE: PRT  
<213> ORGANISM: Homo sapiens

<400> SEQUENCE: 2

Met Lys Arg Pro Ser Ile Lys Arg Ser Leu Leu Gln His Leu Ile Gly
 1               5                  10                  15

Leu Ala Leu Gln Ser Leu Leu Gln His Leu Ile Gly Leu Ser Asn Leu
            20                  25                  30

Thr His Val Leu Tyr Pro Val Pro Leu Glu Ser Tyr Glu Asp Ile His
            35                  40                  45

Gly Thr Leu His Leu Glu Arg Leu Ala Tyr Leu His Ala Arg Leu Arg
        50                  55                  60

Glu Leu Leu Cys Glu Leu Gly Arg Pro Ser Met Val Trp Leu Ser Ala
65                  70                  75                  80

Asn Pro Cys Pro His Cys Gly Asp Arg Thr Phe Tyr Asp Pro Glu Pro
                85                  90                  95

Ile Leu Cys Pro Cys Phe Met Pro Asn Lys Leu Asn Leu Leu His Glu
            100                 105                 110

Thr Asp Ser Ala Val Ala Thr Ala Arg Arg Pro Arg Trp Leu Cys Ala
        115                 120                 125

Gly Ala Leu Val Leu Ala Gly Gly Phe Phe Leu Leu Gly Phe Leu Phe
130                 135                 140

Gly Trp Phe Ile Lys Ser Ala Gln Leu Ala Gly Ala Lys Gly Val Ile
145                 150                 155                 160

Leu Tyr Ser Asp Pro Ala Asp Tyr Phe Ala Pro Gly Val Lys Ser Tyr
            165                 170                 175

Pro Asp Gly Trp Asn Leu Pro Gly Gly Val Gln Arg Gly Asn Ile
        180                 185                 190

Leu Asn Leu Asn Gly Ala Gly Asp Pro Leu Thr Pro Gly Tyr Pro Ala
        195                 200                 205

Asn Glu Tyr Ala Tyr Arg Arg Gly Ile Ala Glu Ala Val Gly Leu Pro
        210                 215                 220

Ser Ile Pro Val His Pro Ile Arg Lys Gly Leu Pro Ser Ile Pro Val
225                 230                 235                 240

His Pro Ile Leu Val Gly Leu Pro Ser Ile Pro Val His Pro Ile Lys
            245                 250                 255

Arg Ile Ser Pro Glu Lys Glu Glu Gln Tyr Ile Ala Lys Arg Gly Leu
            260                 265                 270

Pro Ser Ile Pro Val His Pro Ile Lys Arg Pro Ser Ile Lys Arg Gly
        275                 280                 285

Leu Pro Ser Ile Pro Val His Pro Val
        290                 295

<210> SEQ ID NO 3
<211> LENGTH: 3884
<212> TYPE: DNA
<213> ORGANISM: Homo sapiens

<400> SEQUENCE: 3
cgttgacatt gattattgac tagttattaa tagtaatcaa ttacggggtc attagttcat    60
agcccatata tggagttccg cgttacataa cttacggtaa atggcccgcc tggctgaccg    120
cccaacgacc cccgcccatt gacgtcaata atgacgtatg ttcccatagt aacgccaata    180
gggactttcc attgacgtca atgggtggag tatttacggt aaactgccca cttggcagta    240
catcaagtgt atcatatgcc aagtacgccc cctattgacg tcaatgacgg taaatggccc    300
gcctggcatt atgcccagta catgacctta tgggactttc ctacttggca gtacatctac    360
gtattagtca tcgctattac catggtgatg cggttttggc agtacatcaa tgggcgtgga    420
tagcggtttg actcacgggg atttccaagt ctccacccca ttgacgtcaa tgggagtttg    480
ttttggcacc aaaatcaacg ggactttcca aaatgtcgta acaactccgc cccattgacg    540
caaatgggcg gtaggcgtgt acggtgggag gtctatataa gcagagctct ctggctaact    600

```
agagaaccca ctgcttactg gcttatcgaa attaatacga ctcactatag ggagacccaa    660
gctggctagc gtttaaactt aagccaccat gaatctcctt cacgaaaccg actcggctgt    720
ggccaccgcg cgccgcccgc gctggctgtg cgctggggcg ctggtgctgg cgggtggctt    780
ctttctcctc ggcttcctct tcgggtggtt tataaaaagc gctcagctgg caggggccaa    840
aggagtcatt ctctactccg accctgctga ctactttgct cctggggtga agtcctatcc    900
agatggttgg aatcttcctg gaggtggtgt ccagcgtgga aatatcctaa atctgaatgg    960
tgcaggagac cctctcacac caggttaccc agcaaatgaa tatgcttata ggcgtggaat   1020
tgcagaggct gttggtcttc caagtattcc tgttcatcct attgccctgc agagtctctt   1080
gcagcacctc atcgggctga gcaatctgac ccacgtgctg tatcctgtcc ccctggagag   1140
ttatgaggac atccatggta ccctccacct ggagaggctt gcctatctgc atgccaggct   1200
cagggagttg ctgtgtgagt tggggcggcc cagcatggtc tggcttagtg ccaacccctg   1260
tcctcactgt ggggacagaa ccttctatga cccggagccc atcctgtgcc cctgtttcat   1320
gcctaacaag cgatcgctcc tgcaacacct catcgggctg ggggacgccg cctacagtct   1380
cctgcaacac ctcatcgggc tgatttcccc ggagaaggaa gagcagtata tcgccagtct   1440
cctgcaacac ctcatcgggc tgaagaggcc aagtattaag aggggtcttc caagtattcc   1500
tgttcatcca gtttagtgag aattctgcag atatccatca cactggcggc cgctcgagtc   1560
tagagggccc gtttaaaccc gctgatcagc ctcgactgtg ccttctagtt gccagccatc   1620
tgttgtttgc ccctcccccg tgccttcctt gaccctggaa ggtgccactc ccactgtcct   1680
ttcctaataa aatgaggaaa ttgcatcgca ttgtctgagt aggtgtcatt ctattctggg   1740
gggtggggtg gggcaggaca gcaaggggga ggattgggaa gacaatagca ggcatgctgg   1800
ggatgcggtg ggctctatgg cttctactgg gcggttttat ggacagcaag cgaaccggaa   1860
ttgccagctg gggcgccctc tggtaaggtt gggaagccct gcaaagtaaa ctggatggct   1920
ttcttgccgc caaggatctg atggcgcagg ggatcaagct ctgatcaaga gacaggatga   1980
ggatcgtttc gcatgattga acaagatgga ttgcacgcag gttctccggc cgcttgggtg   2040
gagaggctat tcggctatga ctgggcacaa cagacaatcg gctgctctga tgccgccgtg   2100
ttccggctgt cagcgcaggg gcgcccggtt ctttttgtca agaccgacct gtccggtgcc   2160
ctgaatgaac tgcaagacga ggcagcgcgg ctatcgtggc tggccacgac gggcgttcct   2220
tgcgcagctg tgctcgacgt tgtcactgaa gcgggaaggg actggctgct attgggcgaa   2280
gtgccggggc aggatctcct gtcatctcac cttgctcctg ccgagaaagt atccatcatg   2340
gctgatgcaa tgcggcggct gcatacgctt gatccggcta cctgcccatt cgaccaccaa   2400
gcgaaacatc gcatcgagcg agcacgtact cggatggaag ccggtcttgt cgatcaggat   2460
gatctggacg aagagcatca ggggctcgcg ccagccgaac tgttcgccag gctcaaggcg   2520
agcatgcccg acggcgagga tctcgtcgtg acccatggcg atgcctgctt gccgaatatc   2580
atggtggaaa atggccgctt ttctggattc atcgactgtg gccggctggg tgtggcggac   2640
cgctatcagg acatagcgtt ggctacccgt gatattgctg aagagcttgg cggcgaatgg   2700
gctgaccgct tcctcgtgct ttacggtatc gccgctcccg attcgcagcg catcgccttc   2760
tatcgccttc ttgacgagtt cttctgaatt attaacgctt acaatttcct gatgcggtat   2820
tttctcctta cgcatctgtg cggtatttca caccgcatca ggtggcactt tcggggaaa    2880 tgtgcgcgga acccctattt gtttattttt ctaaatacat tcaaatatgt atccgctcat   2940
gagacaataa ccctgataaa tgcttcaata atagcacgtg ctaaaacttc atttttaatt   3000
```

```
taaaaggatc taggtgaaga tccttttga atctccgg aagagtcaag aacatgtgag    3060
caaaaggcca gcaaaaggcc aggaaccgta aaaaggccgc gttgctggcg ttttttccata  3120 ggctccgccc ccctgacgag catcacaaaa atcgacgctc aagtcagagg tggcgaaacc  3180
cgacaggact ataaagatac caggcgtttc ccctggaag ctccctcgtg cgctctcctg    3240
ttccgaccct gccgcttacc ggatacctgt ccgcctttct cccttcggga agcgtggcgc  3300
tttctcatag ctcacgctgt aggtatctca gttcggtgta ggtcgttcgc tccaagctgg  3360
gctgtgtgca cgaaccccc gttcagcccg accgctgcgc cttatccggt aactatcgtc    3420
ttgagtccaa cccggtaaga cacgacttat cgccactggc agcagccact ggtaacagga  3480
ttagcagagc gaggtatgta ggcggtgcta cagagttctt gaagtggtgg cctaactacg  3540
gctacactag aagaacagta tttggtatct gcgctctgct gaagccagtt accttcggaa  3600
aaagagttgg tagctcttga tccggcaaac aaaccaccgc tggtagcggt ggttttttg    3660 tttgcaagca gcagattacg cgcagaaaaa aaggatctca agaagatcct ttgatctttt    3720
ctacggggtc tgacgctcag tggaacgaaa actcacgtta agggattttg gtccggccgg   3780
aaacgtttgg ttgctgacta attgagatgc atgctttgca tacttctgcc tgctggggag   3840
cctggggact ttccacacct cgcgatgtac gggccagata tacg                    3884
```

<210> SEQ ID NO 4
<211> LENGTH: 275
<212> TYPE: PRT
<213> ORGANISM: Homo sapiens

<400> SEQUENCE: 4

```
Met Asn Leu Leu His Glu Thr Asp Ser Ala Val Ala Thr Ala Arg Arg
  1               5                  10                  15

Pro Arg Trp Leu Cys Ala Gly Ala Leu Val Leu Ala Gly Gly Phe Phe
             20                  25                  30

Leu Leu Gly Phe Leu Phe Gly Trp Phe Ile Lys Ser Ala Gln Leu Ala
         35                  40                  45

Gly Ala Lys Gly Val Ile Leu Tyr Ser Asp Pro Ala Asp Tyr Phe Ala
     50                  55                  60

Pro Gly Val Lys Ser Tyr Pro Asp Gly Trp Asn Leu Pro Gly Gly Gly
 65                  70                  75                  80

Val Gln Arg Gly Asn Ile Leu Asn Leu Asn Gly Ala Gly Asp Pro Leu
                 85                  90                  95

Thr Pro Gly Tyr Pro Ala Asn Glu Tyr Ala Tyr Arg Arg Gly Ile Ala
            100                 105                 110

Glu Ala Val Gly Leu Pro Ser Ile Pro Val His Pro Ile Ala Leu Gln
        115                 120                 125

Ser Leu Leu Gln His Leu Ile Gly Leu Ser Asn Leu Thr His Val Leu
    130                 135                 140

Tyr Pro Val Pro Leu Glu Ser Tyr Glu Asp Ile His Gly Thr Leu His
145                 150                 155                 160

Leu Glu Arg Leu Ala Tyr Leu His Ala Arg Leu Arg Glu Leu Leu Cys
                165                 170                 175

Glu Leu Gly Arg Pro Ser Met Val Trp Leu Ser Ala Asn Pro Cys Pro
            180                 185                 190

His Cys Gly Asp Arg Thr Phe Tyr Asp Pro Glu Pro Ile Leu Cys Pro
        195                 200                 205

Cys Phe Met Pro Asn Lys Arg Ser Leu Leu Gln His Leu Ile Gly Leu
    210                 215                 220
```

Gly Asp Ala Ala Tyr Ser Leu Leu Gln His Leu Ile Gly Leu Ile Ser
225                 230                 235                 240

Pro Glu Lys Glu Gln Tyr Ile Ala Ser Leu Leu Gln His Leu Ile
            245                 250                 255

Gly Leu Lys Arg Pro Ser Ile Lys Arg Gly Leu Pro Ser Ile Pro Val
            260                 265                 270

His Pro Val
    275

<210> SEQ ID NO 5
<211> LENGTH: 9
<212> TYPE: PRT
<213> ORGANISM: Homo sapiens

<400> SEQUENCE: 5

Ser Leu Leu Gln His Leu Ile Gly Leu
1               5

<210> SEQ ID NO 6
<211> LENGTH: 10
<212> TYPE: PRT
<213> ORGANISM: Homo sapiens

<400> SEQUENCE: 6

Gly Leu Pro Ser Ile Pro Val His Pro Ile
1               5                   10

<210> SEQ ID NO 7
<211> LENGTH: 10
<212> TYPE: PRT
<213> ORGANISM: Homo sapiens

<400> SEQUENCE: 7

Gly Leu Pro Ser Ile Pro Val His Pro Val
1               5                   10

<210> SEQ ID NO 8
<211> LENGTH: 66
<212> TYPE: PRT
<213> ORGANISM: Homo sapiens

<400> SEQUENCE: 8

Arg Lys Gly Leu Pro Ser Ile Pro Val His Pro Ile Leu Val Gly Leu
1               5                   10                  15

Pro Ser Ile Pro Val His Pro Ile Lys Arg Ile Ser Pro Glu Lys Glu
            20                  25                  30

Glu Gln Tyr Ile Ala Lys Arg Gly Leu Pro Ser Ile Pro Val His Pro
            35                  40                  45

Ile Lys Arg Pro Ser Ile Lys Arg Gly Leu Pro Ser Ile Pro Val His
    50                  55                  60

Pro Val
65

<210> SEQ ID NO 9
<211> LENGTH: 62
<212> TYPE: PRT
<213> ORGANISM: Homo sapiens

<400> SEQUENCE: 9

Lys Arg Ser Leu Leu Gln His Leu Ile Gly Leu Gly Asp Ala Ala Tyr
1               5                   10                  15

Ser Leu Leu Gln His Leu Ile Gly Leu Ile Ser Pro Glu Lys Glu Glu

```
                    20                  25                  30

Gln Tyr Ile Ala Ser Leu Leu Gln His Leu Ile Gly Leu Lys Arg Pro
                35                  40                  45

Ser Ile Lys Arg Gly Leu Pro Ser Ile Pro Val His Pro Val
            50                  55                  60

<210> SEQ ID NO 10
<211> LENGTH: 150
<212> TYPE: PRT
<213> ORGANISM: Homo sapiens

<400> SEQUENCE: 10

Met Ala Leu Gln Ser Leu Leu Gln His Leu Ile Gly Leu Ser Asn Leu
 1               5                  10                  15

Thr His Val Leu Tyr Pro Val Pro Leu Glu Ser Tyr Glu Asp Ile His
                20                  25                  30

Gly Thr Leu His Leu Glu Arg Leu Ala Tyr Leu His Ala Arg Leu Arg
            35                  40                  45

Glu Leu Leu Cys Glu Leu Gly Arg Pro Ser Met Val Trp Leu Ser Ala
        50                  55                  60

Asn Pro Cys Pro His Cys Gly Asp Arg Thr Phe Tyr Asp Pro Glu Pro
65                  70                  75                  80

Ile Leu Cys Pro Cys Phe Met Pro Asn Lys Arg Ser Leu Leu Gln His
                85                  90                  95

Leu Ile Gly Leu Gly Asp Ala Ala Tyr Ser Leu Leu Gln His Leu Ile
            100                 105                 110

Gly Leu Ile Ser Pro Glu Lys Glu Glu Gln Tyr Ile Ala Ser Leu Leu
        115                 120                 125

Gln His Leu Ile Gly Leu Lys Arg Pro Ser Ile Lys Arg Ser Leu Leu
    130                 135                 140

Gln His Leu Ile Gly Leu
145                 150

<210> SEQ ID NO 11
<211> LENGTH: 191
<212> TYPE: PRT
<213> ORGANISM: Homo sapiens

<400> SEQUENCE: 11

Met Asn Leu Leu His Glu Thr Asp Ser Ala Val Ala Thr Ala Arg Arg
 1               5                  10                  15

Pro Arg Trp Leu Cys Ala Gly Ala Leu Val Leu Ala Gly Gly Phe Phe
                20                  25                  30

Leu Leu Gly Phe Leu Phe Gly Trp Phe Ile Lys Ser Ala Gln Leu Ala
            35                  40                  45

Gly Ala Lys Gly Val Ile Leu Tyr Ser Asp Pro Ala Asp Tyr Phe Ala
        50                  55                  60

Pro Gly Val Lys Ser Tyr Pro Asp Gly Trp Asn Leu Pro Gly Gly Gly
65                  70                  75                  80

Val Gln Arg Gly Asn Ile Leu Asn Leu Asn Gly Ala Gly Asp Pro Leu
                85                  90                  95

Thr Pro Gly Tyr Pro Ala Asn Glu Tyr Ala Tyr Arg Arg Gly Ile Ala
            100                 105                 110

Glu Ala Val Gly Leu Pro Ser Ile Pro Val His Pro Ile Arg Lys Gly
        115                 120                 125

Leu Pro Ser Ile Pro Val His Pro Ile Leu Val Gly Leu Pro Ser Ile
    130                 135                 140
```

Pro Val His Pro Ile Lys Arg Ile Ser Pro Glu Lys Glu Gln Tyr
145                 150                 155                 160

Ile Ala Lys Arg Gly Leu Pro Ser Ile Pro Val His Pro Ile Lys Arg
            165                 170                 175

Pro Ser Ile Lys Arg Gly Leu Pro Ser Ile Pro Val His Pro Ile
        180                 185                 190

<210> SEQ ID NO 12
<211> LENGTH: 328
<212> TYPE: PRT
<213> ORGANISM: Homo sapiens

<400> SEQUENCE: 12

Met Ile Ser Pro Glu Lys Glu Gln Tyr Ile Ala Ser Leu Leu Gln
1               5                   10                  15

His Leu Ile Gly Leu Lys Arg Ser Leu Leu Gln His Leu Ile Gly Leu
            20                  25                  30

Lys Arg Pro Ser Ile Lys Arg Ser Leu Leu Gln His Leu Ile Gly Leu
        35                  40                  45

Ala Leu Gln Ser Leu Leu Gln His Leu Ile Gly Leu Ser Asn Leu Thr
50                  55                  60

His Val Leu Tyr Pro Val Pro Leu Glu Ser Tyr Glu Asp Ile His Gly
65                  70                  75                  80

Thr Leu His Leu Glu Arg Leu Ala Tyr Leu His Ala Arg Leu Arg Glu
                85                  90                  95

Leu Leu Cys Glu Leu Gly Arg Pro Ser Met Val Trp Leu Ser Ala Asn
            100                 105                 110

Pro Cys Pro His Cys Gly Asp Arg Thr Phe Tyr Asp Pro Glu Pro Ile
        115                 120                 125

Leu Cys Pro Cys Phe Met Pro Asn Lys Leu Asn Leu Leu His Glu Thr
130                 135                 140

Asp Ser Ala Val Ala Thr Ala Arg Arg Pro Arg Trp Leu Cys Ala Gly
145                 150                 155                 160

Ala Leu Val Leu Ala Gly Gly Phe Phe Leu Leu Gly Phe Leu Phe Gly
                165                 170                 175

Trp Phe Ile Lys Ser Ala Gln Leu Ala Gly Ala Lys Gly Val Ile Leu
            180                 185                 190

Tyr Ser Asp Pro Ala Asp Tyr Phe Ala Pro Gly Val Lys Ser Tyr Pro
        195                 200                 205

Asp Gly Trp Asn Leu Pro Gly Gly Val Gln Arg Gly Asn Ile Leu
210                 215                 220

Asn Leu Asn Gly Ala Gly Asp Pro Leu Thr Pro Gly Tyr Pro Ala Asn
225                 230                 235                 240

Glu Tyr Ala Tyr Arg Arg Gly Ile Ala Glu Ala Val Gly Leu Pro Ser
                245                 250                 255

Ile Pro Val His Pro Ile Arg Lys Gly Leu Pro Ser Ile Pro Val His
            260                 265                 270

Pro Ile Leu Val Gly Leu Pro Ser Ile Pro Val His Pro Ile Lys Arg
        275                 280                 285

Ile Ser Pro Glu Lys Glu Glu Gln Tyr Ile Ala Lys Arg Gly Leu Pro
290                 295                 300

Ser Ile Pro Val His Pro Ile Lys Arg Pro Ser Ile Lys Arg Gly Leu
305                 310                 315                 320

Pro Ser Ile Pro Val His Pro Ile
                325

<210> SEQ ID NO 13
<211> LENGTH: 297
<212> TYPE: PRT
<213> ORGANISM: Homo sapiens

<400> SEQUENCE: 13

Met Lys Arg Pro Ser Ile Lys Arg Ser Leu Leu Gln His Leu Ile Gly
1               5                   10                  15

Leu Ala Leu Gln Ser Leu Leu Gln His Leu Ile Gly Leu Ser Asn Leu
            20                  25                  30

Thr His Val Leu Tyr Pro Val Pro Leu Glu Ser Tyr Glu Asp Ile His
        35                  40                  45

Gly Thr Leu His Leu Glu Arg Leu Ala Tyr Leu His Ala Arg Leu Arg
    50                  55                  60

Glu Leu Leu Cys Glu Leu Gly Arg Pro Ser Met Val Trp Leu Ser Ala
65                  70                  75                  80

Asn Pro Cys Pro His Cys Gly Asp Arg Thr Phe Tyr Asp Pro Glu Pro
                85                  90                  95

Ile Leu Cys Pro Cys Phe Met Pro Asn Lys Leu Asn Leu His Glu
            100                 105                 110

Thr Asp Ser Ala Val Ala Thr Ala Arg Arg Pro Arg Trp Leu Cys Ala
        115                 120                 125

Gly Ala Leu Val Leu Ala Gly Phe Phe Leu Leu Gly Phe Leu Phe
    130                 135                 140

Gly Trp Phe Ile Lys Ser Ala Gln Leu Ala Gly Ala Lys Gly Val Ile
145                 150                 155                 160

Leu Tyr Ser Asp Pro Ala Asp Tyr Phe Ala Pro Gly Val Lys Ser Tyr
                165                 170                 175

Pro Asp Gly Trp Asn Leu Pro Gly Gly Val Gln Arg Gly Asn Ile
            180                 185                 190

Leu Asn Leu Asn Gly Ala Gly Asp Pro Leu Thr Pro Gly Tyr Pro Ala
        195                 200                 205

Asn Glu Tyr Ala Tyr Arg Arg Gly Ile Ala Glu Ala Val Gly Leu Pro
    210                 215                 220

Ser Ile Pro Val His Pro Ile Arg Lys Gly Leu Pro Ser Ile Pro Val
225                 230                 235                 240

His Pro Ile Leu Val Gly Leu Pro Ser Ile Pro Val His Pro Ile Lys
                245                 250                 255

Arg Ile Ser Pro Glu Lys Glu Glu Gln Tyr Ile Ala Lys Arg Gly Leu
            260                 265                 270

Pro Ser Ile Pro Val His Pro Ile Lys Arg Pro Ser Ile Lys Arg Gly
        275                 280                 285

Leu Pro Ser Ile Pro Val His Pro Val
    290                 295

<210> SEQ ID NO 14
<211> LENGTH: 304
<212> TYPE: PRT
<213> ORGANISM: Homo sapiens

<400> SEQUENCE: 14

Met Ile Ser Pro Glu Lys Glu Glu Gln Tyr Ile Ala Ser Leu Leu Gln
1               5                   10                  15

His Leu Ile Gly Leu Lys Arg Pro Ser Ile Lys Arg Ser Leu Leu Gln
            20                  25                  30

His Leu Ile Gly Leu Ala Leu Gln Ser Leu Leu Gln His Leu Ile Gly
            35                  40                  45

Leu Ser Asn Leu Thr His Val Leu Tyr Pro Val Pro Leu Glu Ser Tyr
 50                  55                  60

Glu Asp Ile His Gly Thr Leu His Leu Glu Arg Leu Ala Tyr Leu His
 65                  70                  75                  80

Ala Arg Leu Arg Glu Leu Leu Cys Glu Leu Gly Arg Pro Ser Met Val
                85                  90                  95

Trp Leu Ser Ala Asn Pro Cys Pro His Cys Gly Asp Arg Thr Phe Tyr
            100                 105                 110

Asp Pro Glu Pro Ile Leu Cys Pro Cys Phe Met Pro Asn Lys Leu Asn
        115                 120                 125

Leu Leu His Glu Thr Asp Ser Ala Val Ala Thr Ala Arg Arg Pro Arg
    130                 135                 140

Trp Cys Ala Gly Ala Leu Val Leu Ala Gly Gly Phe Phe Leu Leu
145                 150                 155                 160

Gly Phe Leu Phe Gly Trp Phe Ile Lys Ser Ala Gln Leu Ala Gly Ala
                165                 170                 175

Lys Gly Val Ile Leu Tyr Ser Asp Pro Ala Asp Tyr Phe Ala Pro Gly
            180                 185                 190

Val Lys Ser Tyr Pro Asp Gly Trp Asn Leu Pro Gly Gly Val Gln
        195                 200                 205

Arg Gly Asn Ile Leu Asn Leu Asn Gly Ala Gly Asp Pro Leu Thr Pro
    210                 215                 220

Gly Tyr Pro Ala Asn Glu Tyr Ala Tyr Arg Arg Gly Ile Ala Glu Ala
225                 230                 235                 240

Val Gly Leu Pro Ser Ile Pro Val His Pro Ile Arg Lys Gly Leu Pro
                245                 250                 255

Ser Ile Pro Val His Pro Ile Leu Val Gly Leu Pro Ser Ile Pro Val
            260                 265                 270

His Pro Val Lys Arg Gly Leu Pro Ser Ile Pro Val His Pro Val Lys
        275                 280                 285

Arg Pro Ser Val Lys Arg Gly Leu Pro Ser Ile Pro Val His Pro Val
    290                 295                 300

<210> SEQ ID NO 15
<211> LENGTH: 288
<212> TYPE: PRT
<213> ORGANISM: Homo sapiens

<400> SEQUENCE: 15

Met Ile Ser Pro Glu Lys Glu Glu Gln Tyr Ile Ala Ser Leu Leu Gln
 1               5                  10                  15

His Leu Ile Gly Leu Ala Leu Gln Ser Leu Leu Gln His Leu Ile Gly
                20                  25                  30

Leu Ser Asn Leu Thr His Val Leu Tyr Pro Val Pro Leu Glu Ser Tyr
            35                  40                  45

Glu Asp Ile His Gly Thr Leu His Leu Glu Arg Leu Ala Tyr Leu His
 50                  55                  60

Ala Arg Leu Arg Glu Leu Leu Cys Glu Leu Gly Arg Pro Ser Met Val
 65                  70                  75                  80

Trp Leu Ser Ala Asn Pro Cys Pro His Cys Gly Asp Arg Thr Phe Tyr
                85                  90                  95

Asp Pro Glu Pro Ile Leu Cys Pro Cys Phe Met Pro Asn Lys Leu Asn
            100                 105                 110

```
Leu Leu His Glu Thr Asp Ser Ala Val Ala Thr Ala Arg Arg Pro Arg
            115                 120                 125

Trp Leu Cys Ala Gly Ala Leu Val Leu Ala Gly Gly Phe Phe Leu Leu
        130                 135                 140

Gly Phe Leu Phe Gly Trp Phe Ile Lys Ser Ala Gln Leu Ala Gly Ala
145                 150                 155                 160

Lys Gly Val Ile Leu Tyr Ser Asp Pro Ala Asp Tyr Phe Ala Pro Gly
                165                 170                 175

Val Lys Ser Tyr Pro Asp Gly Trp Asn Leu Pro Gly Gly Val Gln
                180                 185                 190

Arg Gly Asn Ile Leu Asn Leu Asn Gly Ala Gly Asp Pro Leu Thr Pro
                195                 200                 205

Gly Tyr Pro Ala Asn Glu Tyr Ala Tyr Arg Arg Gly Ile Ala Glu Ala
        210                 215                 220

Val Gly Leu Pro Ser Ile Pro Val His Pro Ile Arg Lys Gly Leu Pro
225                 230                 235                 240

Ser Ile Pro Val His Pro Ile Leu Val Gly Leu Pro Ser Ile Pro Val
                245                 250                 255

His Pro Val Lys Arg Gly Leu Pro Ser Ile Pro Val His Pro Val Lys
                260                 265                 270

Arg Pro Ser Val Lys Arg Gly Leu Pro Ser Ile Pro Val His Pro Val
                275                 280                 285

<210> SEQ ID NO 16
<211> LENGTH: 308
<212> TYPE: PRT
<213> ORGANISM: Homo sapiens

<400> SEQUENCE: 16

Met Lys Arg Ser Leu Leu Gln His Leu Ile Gly Leu Lys Arg Pro Ser
 1               5                  10                  15

Ile Lys Arg Ser Leu Leu Gln His Leu Ile Gly Leu Ala Leu Gln Ser
                20                  25                  30

Leu Leu Gln His Leu Ile Gly Leu Ser Asn Leu Thr His Val Leu Tyr
            35                  40                  45

Pro Val Pro Leu Glu Ser Tyr Glu Asp Ile His Gly Thr Leu His Leu
        50                  55                  60

Glu Arg Leu Ala Tyr Leu His Ala Arg Leu Arg Glu Leu Leu Cys Glu
 65                 70                  75                  80

Leu Gly Arg Pro Ser Met Val Trp Leu Ser Ala Asn Pro Cys Pro His
                85                  90                  95

Cys Gly Asp Arg Thr Phe Tyr Asp Pro Glu Pro Ile Leu Cys Pro Cys
                100                 105                 110

Phe Met Pro Asn Lys Leu Asn Leu Leu His Glu Thr Asp Ser Ala Val
        115                 120                 125

Ala Thr Ala Arg Arg Pro Arg Trp Leu Cys Ala Gly Ala Leu Val Leu
        130                 135                 140

Ala Gly Gly Phe Phe Leu Leu Gly Phe Leu Phe Gly Trp Phe Ile Lys
145                 150                 155                 160

Ser Ala Gln Leu Ala Gly Ala Lys Gly Val Ile Leu Tyr Ser Asp Pro
                165                 170                 175

Ala Asp Tyr Phe Ala Pro Gly Val Lys Ser Tyr Pro Asp Gly Trp Asn
                180                 185                 190

Leu Pro Gly Gly Val Gln Arg Gly Asn Ile Leu Asn Leu Asn Gly
                195                 200                 205
```

```
Ala Gly Asp Pro Leu Thr Pro Gly Tyr Pro Ala Asn Glu Tyr Ala Tyr
    210                 215                 220

Arg Arg Gly Ile Ala Glu Ala Val Gly Leu Pro Ser Ile Pro Val His
225                 230                 235                 240

Pro Ile Arg Lys Gly Leu Pro Ser Ile Pro Val His Pro Val Leu Val
                245                 250                 255

Gly Leu Pro Ser Ile Pro Val His Pro Val Lys Arg Ile Ser Pro Glu
            260                 265                 270

Lys Glu Glu Gln Tyr Ile Ala Lys Arg Gly Leu Pro Ser Ile Pro Val
        275                 280                 285

His Pro Ile Lys Arg Pro Ser Ile Lys Arg Gly Leu Pro Ser Ile Pro
    290                 295                 300

Val His Pro Val
305
```

<210> SEQ ID NO 17
<211> LENGTH: 275
<212> TYPE: PRT
<213> ORGANISM: Homo sapiens

<400> SEQUENCE: 17

```
Met Asn Leu Leu His Glu Thr Asp Ser Ala Val Ala Thr Ala Arg Arg
  1               5                  10                  15

Pro Arg Trp Leu Cys Ala Gly Ala Leu Val Leu Ala Gly Gly Phe Phe
                 20                  25                  30

Leu Leu Gly Phe Leu Phe Gly Trp Phe Ile Lys Ser Ala Gln Leu Ala
             35                  40                  45

Gly Ala Lys Gly Val Ile Leu Tyr Ser Asp Pro Ala Asp Tyr Phe Ala
 50                  55                  60

Pro Gly Val Lys Ser Tyr Pro Asp Gly Trp Asn Leu Pro Gly Gly Gly
 65                  70                  75                  80

Val Gln Arg Gly Asn Ile Leu Asn Leu Asn Gly Ala Gly Asp Pro Leu
                 85                  90                  95

Thr Pro Gly Tyr Pro Ala Asn Glu Tyr Ala Tyr Arg Arg Gly Ile Ala
            100                 105                 110

Glu Ala Val Gly Leu Pro Ser Ile Pro Val His Pro Ile Ala Leu Gln
        115                 120                 125

Ser Leu Leu Gln His Leu Ile Gly Leu Ser Asn Leu Thr His Val Leu
130                 135                 140

Tyr Pro Val Pro Leu Glu Ser Tyr Glu Asp Ile His Gly Thr Leu His
145                 150                 155                 160

Leu Glu Arg Leu Ala Tyr Leu His Ala Arg Leu Arg Glu Leu Leu Cys
                165                 170                 175

Glu Leu Gly Arg Pro Ser Met Val Trp Leu Ser Ala Asn Pro Cys Pro
            180                 185                 190

His Cys Gly Asp Arg Thr Phe Tyr Asp Pro Glu Pro Ile Leu Cys Pro
        195                 200                 205

Cys Phe Met Pro Asn Lys Arg Ser Leu Leu Gln His Leu Ile Gly Leu
    210                 215                 220

Gly Asp Ala Ala Tyr Ser Leu Leu Gln His Leu Ile Gly Leu Ile Ser
225                 230                 235                 240

Pro Glu Lys Glu Glu Gln Tyr Ile Ala Ser Leu Leu Gln His Leu Ile
                245                 250                 255

Gly Leu Lys Arg Pro Ser Ile Lys Arg Gly Leu Pro Ser Ile Pro Val
            260                 265                 270
```

```
His Pro Val
    275

<210> SEQ ID NO 18
<211> LENGTH: 296
<212> TYPE: PRT
<213> ORGANISM: Homo sapiens

<400> SEQUENCE: 18

Met Lys Arg Ser Leu Leu Gln His Leu Ile Gly Leu Lys Arg Pro Ser
1               5                   10                  15

Ile Lys Arg Ser Leu Leu Gln His Leu Ile Gly Leu Ala Leu Gln Ser
            20                  25                  30

Leu Leu Gln His Leu Ile Gly Leu Ser Asn Leu Thr His Val Leu Tyr
        35                  40                  45

Pro Val Pro Leu Glu Ser Tyr Glu Asp Ile His Gly Thr Leu His Leu
    50                  55                  60

Glu Arg Leu Ala Tyr Leu His Ala Arg Leu Arg Glu Leu Leu Cys Glu
65                  70                  75                  80

Leu Gly Arg Pro Ser Met Val Trp Leu Ser Ala Asn Pro Cys Pro His
                85                  90                  95

Cys Gly Asp Arg Thr Phe Tyr Asp Pro Glu Pro Ile Leu Cys Pro Cys
            100                 105                 110

Phe Met Pro Asn Lys Leu Asn Leu His Glu Thr Asp Ser Ala Val
        115                 120                 125

Ala Thr Ala Arg Arg Pro Arg Trp Leu Cys Ala Gly Ala Leu Val Leu
    130                 135                 140

Ala Gly Gly Phe Phe Leu Leu Gly Phe Leu Phe Gly Trp Phe Ile Lys
145                 150                 155                 160

Ser Ala Gln Leu Ala Gly Ala Lys Gly Val Ile Leu Tyr Ser Asp Pro
                165                 170                 175

Ala Asp Tyr Phe Ala Pro Gly Val Lys Ser Tyr Pro Asp Gly Trp Asn
            180                 185                 190

Leu Pro Gly Gly Gly Val Gln Arg Gly Asn Ile Leu Asn Leu Asn Gly
        195                 200                 205

Ala Gly Asp Pro Leu Thr Pro Gly Tyr Pro Ala Asn Glu Tyr Ala Tyr
    210                 215                 220

Arg Arg Gly Ile Ala Glu Ala Val Gly Leu Pro Ser Ile Pro Val His
225                 230                 235                 240

Pro Val Leu Val Gly Leu Pro Ser Ile Pro Val His Pro Val Lys Arg
                245                 250                 255

Ile Ser Pro Glu Lys Glu Glu Gln Tyr Ile Ala Lys Arg Gly Leu Pro
            260                 265                 270

Ser Ile Pro Val His Pro Ile Lys Arg Pro Ser Ile Lys Arg Gly Leu
        275                 280                 285

Pro Ser Ile Pro Val His Pro Val
    290                 295

<210> SEQ ID NO 19
<211> LENGTH: 750
<212> TYPE: PRT
<213> ORGANISM: Homo sapiens

<400> SEQUENCE: 19

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
```

```
                    20                  25                  30
Phe Leu Leu Gly Phe Leu Phe Gly Trp Phe Ile Lys Ser Ser Asn Glu
                35                  40                  45
Ala Thr Asn Ile Thr Pro Lys His Asn Met Lys Ala Phe Leu Asp Glu
 50                  55                  60
Leu Lys Ala Glu Asn Ile Lys Lys Phe Leu Tyr Asn Phe Thr Gln Ile
 65                  70                  75                  80
Pro His Leu Ala Gly Thr Glu Gln Asn Phe Gln Leu Ala Lys Gln Ile
                 85                  90                  95
Gln Ser Gln Trp Lys Glu Phe Gly Leu Asp Ser Val Glu Leu Ala His
                100                 105                 110
Tyr Asp Val Leu Leu Ser Tyr Pro Asn Lys Thr His Pro Asn Tyr Ile
                115                 120                 125
Ser Ile Ile Asn Glu Asp Gly Asn Glu Ile Phe Asn Thr Ser Leu Phe
                130                 135                 140
Glu Pro Pro Pro Gly Tyr Glu Asn Val Ser Asp Ile Val Pro Pro
145                 150                 155                 160
Phe Ser Ala Phe Ser Pro Gln Gly Met Pro Glu Gly Asp Leu Val Tyr
                165                 170                 175
Val Asn Tyr Ala Arg Thr Glu Asp Phe Phe Lys Leu Glu Arg Asp Met
                180                 185                 190
Lys Ile Asn Cys Ser Gly Lys Ile Val Ile Ala Arg Tyr Gly Lys Val
                195                 200                 205
Phe Arg Gly Asn Lys Val Lys Asn Ala Gln Leu Ala Gly Ala Lys Gly
                210                 215                 220
Val Ile Leu Tyr Ser Asp Pro Ala Asp Tyr Phe Ala Pro Gly Val Lys
225                 230                 235                 240
Ser Tyr Pro Asp Gly Trp Asn Leu Pro Gly Gly Val Gln Arg Gly
                245                 250                 255
Asn Ile Leu Asn Leu Asn Gly Ala Gly Asp Pro Leu Thr Pro Gly Tyr
                260                 265                 270
Pro Ala Asn Glu Tyr Ala Tyr Arg Arg Gly Ile Ala Glu Ala Val Gly
                275                 280                 285
Leu Pro Ser Ile Pro Val His Pro Ile Gly Tyr Tyr Asp Ala Gln Lys
                290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
                340                 345                 350
Thr Arg Ile Tyr Asn Val Ile Gly Thr Leu Arg Gly Ala Val Glu Pro
                355                 360                 365
Asp Arg Tyr Val Ile Leu Gly Gly His Arg Asp Ser Trp Val Phe Gly
                370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
                420                 425                 430
Glu Trp Ala Glu Glu Asn Ser Arg Leu Leu Gln Glu Arg Gly Val Ala
                435                 440                 445
```

```
Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
                595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
                675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750

<210> SEQ ID NO 20
<211> LENGTH: 509
<212> TYPE: PRT
<213> ORGANISM: Homo sapiens

<400> SEQUENCE: 20

Met Glu Arg Arg Arg Leu Trp Gly Ser Ile Gln Ser Arg Tyr Ile Ser
 1               5                  10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80
```

-continued

```
Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Ser His Ile His Ala
            260                 265                 270

Ser Ser Tyr Ile Ser Pro Glu Lys Glu Gln Tyr Ile Ala Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505
```

```
<210> SEQ ID NO 21
<211> LENGTH: 88
<212> TYPE: PRT
<213> ORGANISM: Homo sapiens

<400> SEQUENCE: 21

Ala Leu Gln Ser Leu Leu Gln His Leu Ile Gly Leu Ser Asn Leu Thr
 1               5                  10                  15

His Val Leu Tyr Pro Val Pro Leu Glu Ser Tyr Glu Asp Ile His Gly
            20                  25                  30

Thr Leu His Leu Glu Arg Leu Ala Tyr Leu His Ala Arg Leu Arg Glu
        35                  40                  45

Leu Leu Cys Glu Leu Gly Arg Pro Ser Met Val Trp Leu Ser Ala Asn
    50                  55                  60

Pro Cys Pro His Cys Gly Asp Arg Thr Phe Tyr Asp Pro Glu Pro Ile
65                  70                  75                  80

Leu Cys Pro Cys Phe Met Pro Asn
                85

<210> SEQ ID NO 22
<211> LENGTH: 43
<212> TYPE: PRT
<213> ORGANISM: Homo sapiens

<400> SEQUENCE: 22

Asn Leu Leu His Glu Thr Asp Ser Ala Val Thr Ala Arg Arg Pro
 1               5                  10                  15

Arg Trp Leu Cys Ala Gly Ala Leu Val Leu Ala Gly Gly Phe Phe Leu
            20                  25                  30

Leu Gly Phe Leu Phe Gly Trp Phe Ile Lys Ser
        35                  40

<210> SEQ ID NO 23
<211> LENGTH: 81
<212> TYPE: PRT
<213> ORGANISM: Homo sapiens

<400> SEQUENCE: 23

Ala Gln Leu Ala Gly Ala Lys Gly Val Ile Leu Tyr Ser Asp Pro Ala
 1               5                  10                  15

Asp Tyr Phe Ala Pro Gly Val Lys Ser Tyr Pro Asp Gly Trp Asn Leu
            20                  25                  30

Pro Gly Gly Gly Val Gln Arg Gly Asn Ile Leu Asn Leu Asn Gly Ala
        35                  40                  45

Gly Asp Pro Leu Thr Pro Gly Tyr Pro Ala Asn Glu Tyr Ala Tyr Arg
    50                  55                  60

Arg Gly Ile Ala Glu Ala Val Gly Leu Pro Ser Ile Pro Val His Pro
65                  70                  75                  80

Ile

<210> SEQ ID NO 24
<211> LENGTH: 81
<212> TYPE: PRT
<213> ORGANISM: Homo sapiens

<400> SEQUENCE: 24

Ala Gln Leu Ala Gly Ala Lys Gly Val Ile Leu Tyr Ser Asp Pro Ala
 1               5                  10                  15
```

```
Asp Tyr Phe Ala Pro Gly Val Lys Ser Tyr Pro Asp Gly Trp Asn Leu
             20                  25                  30

Pro Gly Gly Gly Val Gln Arg Gly Asn Ile Leu Asn Leu Asn Gly Ala
         35                  40                  45

Gly Asp Pro Leu Thr Pro Gly Tyr Pro Ala Asn Glu Tyr Ala Tyr Arg
 50                  55                  60

Arg Gly Ile Ala Glu Ala Val Gly Leu Pro Ser Ile Pro Val His Pro
 65                  70                  75                  80

Val
```

<210> SEQ ID NO 25
<211> LENGTH: 17
<212> TYPE: PRT
<213> ORGANISM: Homo sapiens

<400> SEQUENCE: 25

```
Met Lys Arg Pro Ser Ile Lys Arg Ser Leu Leu Gln His Leu Ile Gly
 1               5                  10                  15

Leu
```

<210> SEQ ID NO 26
<211> LENGTH: 22
<212> TYPE: PRT
<213> ORGANISM: Homo sapiens

<400> SEQUENCE: 26

```
Ala Leu Gln Ser Leu Leu Gln His Leu Ile Gly Leu Ser Asn Leu Thr
 1               5                  10                  15

His Val Leu Tyr Pro Val
             20
```

<210> SEQ ID NO 27
<211> LENGTH: 29
<212> TYPE: PRT
<213> ORGANISM: Homo sapiens

<400> SEQUENCE: 27

```
Arg Leu Ala Tyr Leu His Ala Arg Leu Arg Glu Leu Leu Cys Glu Leu
 1               5                  10                  15

Gly Arg Pro Ser Met Val Trp Leu Ser Ala Asn Pro Cys
             20                  25
```

<210> SEQ ID NO 28
<211> LENGTH: 11
<212> TYPE: PRT
<213> ORGANISM: Homo sapiens

<400> SEQUENCE: 28

```
Ile Ser Pro Glu Lys Glu Glu Gln Tyr Ile Ala
 1               5                  10
```

<210> SEQ ID NO 29
<211> LENGTH: 32
<212> TYPE: PRT
<213> ORGANISM: Homo sapiens

<400> SEQUENCE: 29

```
Asp Pro Leu Thr Pro Gly Tyr Pro Ala Asn Glu Tyr Ala Tyr Arg Arg
 1               5                  10                  15

Gly Ile Ala Glu Ala Val Gly Leu Pro Ser Ile Pro Val His Pro Ile
             20                  25                  30
```

```
<210> SEQ ID NO 30
<211> LENGTH: 9
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: Xaa = Nva
<220> FEATURE:
<221> NAME/KEY: VARIANT
<222> LOCATION: (9)...(9)
<223> OTHER INFORMATION: Xaa = Nle
<220> FEATURE:
<223> OTHER INFORMATION: Analog of MHC class I-restricted T cell epitope

<400> SEQUENCE: 30

Ser Xaa Leu Gly His Leu Ile Gly Xaa
 1               5
```